(12) United States Patent
Miyawaki et al.

(10) Patent No.: US 7,960,530 B2
(45) Date of Patent: Jun. 14, 2011

(54) FLUORESCENT PROTEIN

(75) Inventors: Atsushi Miyawaki, Saitama (JP);
Hidekazu Tsutsui, Saitama (JP);
Satoshi Karasawa, Tokyo (JP)

(73) Assignee: Riken, Saitama (JP)

( * ) Notice: Subject to any disclaimer, the term of this patent is extended or adjusted under 35 U.S.C. 154(b) by 1009 days.

(21) Appl. No.: 10/561,040

(22) PCT Filed: Jun. 16, 2004

(86) PCT No.: PCT/JP2004/008790
§ 371 (c)(1),
(2), (4) Date: Oct. 16, 2006

(87) PCT Pub. No.: WO2004/111236
PCT Pub. Date: Dec. 23, 2004

(65) Prior Publication Data
US 2007/0072259 A1    Mar. 29, 2007

(30) Foreign Application Priority Data
Jun. 16, 2003    (JP) .................. 2003-170330

(51) Int. Cl.
*C07H 21/04* (2006.01)
*C12P 21/06* (2006.01)
(52) U.S. Cl. ... 536/23.5; 530/350; 435/69.1; 435/320.1; 435/325
(58) Field of Classification Search .................. 536/23.5; 530/350; 435/69.1, 320.1, 325
See application file for complete search history.

(56) References Cited

U.S. PATENT DOCUMENTS

| | | | |
|---|---|---|---|
| 2003/0157643 A1* | 8/2003 | Almond et al. | 435/69.1 |
| 2005/0032085 A1 | 2/2005 | Labas et al. | |
| 2005/0106661 A1 | 5/2005 | Miyawaki et al. | |
| 2006/0154296 A1 | 7/2006 | Miyawaki et al. | |
| 2006/0240472 A1 | 10/2006 | Miyawaki et al. | |

FOREIGN PATENT DOCUMENTS

| | | |
|---|---|---|
| WO | 02/42323 | 5/2002 |
| WO | 03/033693 | 4/2003 |
| WO | 03/042401 | 5/2003 |
| WO | 03/054191 | 7/2003 |
| WO | 03/104460 | 12/2003 |
| WO | 03/104461 | 12/2003 |
| WO | 2004/018671 | 3/2004 |
| WO | 2004/111235 | 12/2004 |
| WO | 2005/054464 | 6/2005 |

OTHER PUBLICATIONS

Gurskaya et al., "Color transitions in coral's fluorescent proteins by site-directed mutagenesis," BMC Biochemistry, vol. 2, No. 6, Jul. 10, 2001, 7 pages.
Labas et al., "Diversity and evolution of the green fluorescent protein family," Proceedings of the National Academy of Sciences U.S.A., vol. 99. No. 7, Apr. 2, 2002, pp. 4256-4261.
Yang et al., "The molecular structure of green fluorescent protein," Nature Biotechnology, vol. 14, No. 10, Oct. 1996, pp. 1246-1251.
Matz et al., "Family of the green fluorescent protein: journey to the end of the rainbow," BioEssays, vol. 24, 2002, pp. 953-959.
Miyawaki, "Green Fluorescent Protein-like Proteins in Reef Anthozoa Animals," Cell Structure and Function, vol. 27, 2002, pp. 343-347.
Campbell et al, "A monomeric red fluorescent protein," Proceedings of the National Academy of Sciences U.S.A., vol. 99, No. 12, Jun. 11, 2002 pp. 7877-7882.
Matz et al, "Fluorescent proteins from nonbioluminescent Anthozoa species," Nature Biotechnology, vol. 17, No. 10, Oct. 1999, pp. 969-973.
Fradkov et al., "Novel fluorescent protein from Discosoma coral and its mutants possesses a unique far-red fluorescence," FEBS Letters, vol. 479, No. 3, Aug. 18, 2000, pp. 127-130.
U.S. Appl. No. 10/492,081 (Miyawaki et al.), filed Oct. 10, 2002.
U.S. Appl. No. 10/498,505 (Miyawaki et al.), filed Dec. 20, 2002.
U.S. Appl. No. 10/525,365 (Miyawaki et al.), filed Aug. 22, 2003.
U.S. Appl. No. 10/561,041 (Miyawaki et al.), filed Jun. 16, 2004.
U.S. Appl. No. 10/581,551 (Miyawaki et al.), filed Dec. 3, 2004.
U.S. Appl. No. 11/390,215 (Miyawaki et al.), filed Mar. 28, 2006.
Tsien, R.Y., "The Green Fluorescent Protein," Annual Review of Biochemistry, vol. 67, 1998, pp. 509-544.

* cited by examiner

*Primary Examiner* — Chih-Min Kam
(74) *Attorney, Agent, or Firm* — Greenblum & Bernstein, P.L.C.

(57) ABSTRACT

An object of the present invention is to provide a novel fluorescent protein derived from *favia favus*. The present invention provides a fluorescent protein derived from *favia favus* having the following properties:
(1) an excitation maximum wavelength is 507 nm;
(2) a fluorescence maximum wavelength is 517 nm;
(3) a molar absorption coefficient at 482 nm is 80,000;
(4) a quantum yield is 0.68; and
(5) pH sensitivity of the fluorescence maximum is stable at pH 5 to pH 11.

3 Claims, 7 Drawing Sheets

FLUORESCENT PROTEIN

This application is the National Stage of PCT/JP2004/008790, filed Jun. 16, 2004.

SEQUENCE LISTING

The instant application contains a Sequence Listing which has been submitted in ASCII format via EFS-Web and is hereby incorporated by reference in its entirety. Said ASCII copy, created on Jan. 5, 2011, is named P28994.txt and is 40,504 bytes in size.

TECHNICAL FIELD

The present invention relates to a novel fluorescent protein. More specifically, the present invention relates to a novel fluorescent protein derived from *favia favus* and the use thereof.

BACKGROUND ART

Green fluorescent protein (GFP) derived from *Aequorea victoria*, a jellyfish, has many purposes in biological systems. Recently, various GFP mutants have been produced based on the random mutagenesis and semi-rational mutagenesis, wherein a color is changed, a folding property is improved, luminance is enhanced, or pH sensitivity is modified. Fluorescent proteins such as GFP are fused with other proteins by gene recombinant technique, and monitoring of the expression and transportation of the fusion proteins is carried out.

One of the most commonly used types of GFP mutant is Yellow fluorescent protein (YFP). Among Aequorea-derived GFP mutants, YFP exhibits the fluorescence with the longest wavelength. The values ε and Φ of the majority of YEPs are 60,000 to 100,000 $M^{-1}cm^{-1}$ and 0.6 to 0.8, respectively (Tsien, R. Y. (1998). Ann. Rev. Biochem. 67, 509-544). These values are comparable to those of the general fluorescent group (fluorescein, rhodamine, etc.). Accordingly, improvement of the absolute luminance of YFP is nearly approaching its limit.

In addition, cyan fluorescent protein (CFP) is another example of the GFP mutant. Of this type of protein, ECFP (enhanced cyan fluorescent protein) has been known. Moreover, red fluorescent protein (RFP) has been isolated from sea anemone (*Discosoma* sp.). Of this type of protein, DsRed has been known. Thus, 4 types of fluorescent proteins, that are, green fluorescent protein, yellow fluorescent protein, cyan fluorescent protein, and red fluorescent protein, have successfully been developed. The range of the spectrum has significantly been expanded.

Also, there are many cnidarians which emit fluorescence. Cloning of genes of fluorescent proteins from cnidarians has been attempted, but cloning of more genes is necessary in order to increase repertoire of fluorescent and biochemical properties.

DISCLOSURE OF THE INVENTION

An object of the present invention is to provide a novel fluorescent protein derived from *favia favus*.

In order to achieve the above object, the present inventors have conducted intensive studies. They have designed adequate primers based on the amino acid sequence information of existing fluorescent proteins, amplified the gene obtained from the cDNA library derived from *favia favus* using the aforementioned primers, and then succeeded in cloning a novel gene encoding a fluorescent protein. Further, the present inventors have analyzed fluorescence properties and pH sensitivity of the obtained fluorescent protein derived from *favia favus*. The present invention has been completed based on such findings.

Thus, the present invention provides a fluorescent protein derived from *favia favus* having the following properties:
(1) an excitation maximum wavelength is 507 nm;
(2) a fluorescence maximum wavelength is 517 nm;
(3) a molar absorption coefficient at 482 nm is 80,000;
(4) a quantum yield is 0.68; and
(5) pH sensitivity of the fluorescence maximum is stable at pH 5 to pH 11.

Another aspect of the present invention provides a fluorescent protein having any of the following amino acid sequences:
(a) an amino acid sequence shown in SEQ ID NO: 1; or
(b) an amino acid sequence comprising a deletion, substitution and/or addition of one or several amino acids with respect to the amino acid sequence shown in SEQ ID NO: 1, and having fluorescent properties.

A further aspect of the present invention provides a fluorescent protein having an amino acid sequence derived from any of the following amino acid sequences by substitution from asparagine to histidine at 62th amino acid reside:
(a) an amino acid sequence shown in SEQ ID NO: 1; or
(b) an amino acid sequence comprising a deletion, substitution and/or addition of one or several amino acids with respect to the amino acid sequence shown in SEQ ID NO: 1, and having fluorescent properties.

A further aspect of the present invention provides a fluorescent protein having an amino acid sequence derived from any of the following amino acid sequences by substitution from methionine to valine at 40th amino acid residue, substitution from aspartic acid to histidine at 62th amino acid residue, and substitution from isoleucine to methionine at 198th amino acid residue.
(a) an amino acid sequence shown in SEQ ID NO: 1; or
(b) an amino acid sequence comprising a deletion, substitution and/or addition of one or several amino acids with respect to the amino acid sequence shown in SEQ ID NO: 1, and having fluorescent properties.

A further aspect of the present invention provides a fluorescent protein having an amino acid sequence derived from any of the following amino acid sequences by substitution from methionine to isoleucine at 10th amino acid residue, substitution from leucine to valine at 12th amino acid residue, substitution from methionine to valine at 40th amino acid residue, substitution from valine to alanine at 60th amino acid residue, substitution from aspartic acid to histidine at 62th amino acid residue, substitution from tyrosine to asparagine at 119th amino acid residue, substitution from proline to serine at 144th amino acid residue, substitution from arginine to leucine at 197th amino acid residue, and substitution from isoleucine to methionine at 198th amino acid residue:
(a) an amino acid sequence shown in SEQ ID NO: 1; or
(b) an amino acid sequence comprising a deletion, substitution and/or addition of one or several amino acids with respect to the amino acid sequence shown in SEQ ID NO: 1, and having fluorescent properties.

A further aspect of the present invention provides a fluorescent protein having an amino acid sequence derived from any of the following amino acid sequences by substitution from methionine to isoleucine at 10th amino acid residue, substitution from methionine to valine at 40th amino acid residue, substitution from valine to alanine at 60th amino acid residue, substitution from aspartic acid to histidine at 62th amino acid residue, substitution from lysine to glutamic acid at 70th amino acid residue, substitution from tyrosine to asparagine at 119th amino acid residue, substitution from arginine to glutamine at 197th amino acid residue, and substitution from isoleucine to methionine at 198th amino acid residue:

(a) an amino acid sequence shown in SEQ ID NO: 1; or (b) an amino acid sequence comprising a deletion, substitution and/or addition of one or several amino acids with respect to the amino acid sequence shown in SEQ ID NO: 1, and having fluorescent properties.

A further aspect of the present invention provides a fluorescent protein having an amino acid sequence derived from any of the following amino acid sequences by substitution from valine to alanine at 60th amino acid residue, substitution from aspartic acid to glycine at 62th amino acid residue, substitution from tyrosine to histidine at 63th amino acid residue, substitution from histidine to leucine at 196th amino acid residue, and substitution from isoleucine to threonine at 198th amino acid residue:

(a) an amino acid sequence shown in SEQ ID NO: 1; or (b) an amino acid sequence comprising a deletion, substitution and/or addition of one or several amino acids with respect to the amino acid sequence shown in SEQ ID NO: 1, and having fluorescent properties.

A further aspect of the present invention provides DNA encoding the protein of the present invention.

A further aspect of the present invention provides any of the following DNA:

(a) DNA encoding the amino acid sequence shown in SEQ ID NO: 1; or (b) DNA encoding an amino acid sequence comprising a deletion, substitution and/or addition of one or several amino acids with respect to the amino acid sequence shown in SEQ ID NO: 1, and encoding a fluorescent protein.

A further aspect of the present invention provides DNA having any of the following nucleotide sequences:

(a) a nucleotide sequence shown in SEQ ID NO: 2; or (b) a nucleotide sequence comprising a deletion, substitution and/or addition of one or several nucleotides with respect of the nucleotide sequence shown in SEQ ID NO: 2, and encoding a fluorescent protein.

A further aspect of the present invention provides DNA comprising any of the following nucleotide sequences:

(a) a nucleotide sequence shown in SEQ ID NO: 13, 15, 17, 19, or 21; or (b) a nucleotide sequence comprising a deletion, substitution and/or addition of one or several nucleotides with respect of the nucleotide sequence shown in SEQ ID NO: 13, 15, 17, 19, or 21, and encoding a fluorescent protein.

In another aspect of the present invention, there is provided a recombinant vector having the DNA of the present invention.

In another aspect of the present invention, there is provided a transformant having the DNA or recombinant vector of the present invention.

In another aspect of the present invention, there is provided a fusion fluorescent protein consisting of the fluorescent proteins of the present invention and another protein.

Preferably, said another protein is one that localizes in the cell, and more preferably one specific to an intracellular organella.

In another aspect of the present invention, there is provided a method for analyzing the localization or dynamics of a protein in cells, characterized in that the fusion protein of the present invention is allowed to be expressed in cells.

In another aspect of the present invention, there is provided a fluorescent reagent kit which comprises any of the fluorescent protein, DNA, recombinant vector, transformant or fusion protein of the present invention.

A further aspect of the present invention provides a method for producing a fluorescent protein capable of green-to-red photoconversion in response to irradiation with light, which comprises introducing substitution from an amino acid corresponding to 62th amino acid residue of the fluorescent protein having the amino acid sequence shown in SEQ ID NO: 1 to histidine into a fluorescent protein incapable of green-to-red photoconversion in response to irradiation with light.

A further aspect of the present invention provides a method for producing a fluorescent protein capable of green-to-red photoconversion in response to irradiation with light, which comprises introducing at least one of the following amino acid substitutions into a fluorescent protein incapable of green-to-red photoconversion in response to irradiation with light;

(1) substitution from an amino acid corresponding to 62th amino acid residue of the fluorescent protein having the amino acid sequence shown in SEQ ID NO: 1 to histidine;

(2) substitution from an amino acid corresponding to 10th amino acid residue of the fluorescent protein having the amino acid sequence shown in SEQ ID NO: 1 to isoleucine;

(3) substitution from an amino acid corresponding to 12th amino acid residue of the fluorescent protein having the amino acid sequence shown in SEQ ID NO: 1 to valine;

(4) substitution from an amino acid corresponding to 40th amino acid residue of the fluorescent protein having the amino acid sequence shown in SEQ ID NO: 1 to valine;

(5) substitution from an amino acid corresponding to 60th amino acid residue of the fluorescent protein having the amino acid sequence shown in SEQ ID NO: 1 to alanine;

(6) substitution from an amino acid corresponding to 70th amino acid residue of the fluorescent protein having the amino acid sequence shown in SEQ ID NO: 1 to glutamic acid;

(7) substitution from an amino acid corresponding to 119th amino acid residue of the fluorescent protein having the amino acid sequence shown in SEQ ID NO: 1 to asparagine;

(8) substitution from an amino acid corresponding to 144th amino acid residue of the fluorescent protein having the amino acid sequence shown in SEQ ID NO: 1 to serine;

(9) substitution from an amino acid corresponding to 197th amino acid residue of the fluorescent protein having the amino acid sequence shown in SEQ ID NO: 1 to leucine or glutamine; or

(10) substitution from an amino acid corresponding to 198th amino acid residue of the fluorescent protein having the amino acid sequence shown in SEQ ID NO: 1 to methionine;

A further aspect of the present invention provides a method for producing a fluorescent protein with an increased rate of green-to-red photoconversion and enhanced fluorescence intensity, which comprises introducing at least one of the following amino acid substitutions in a fluorescent protein:

(1) substitution from an amino acid corresponding to 62th amino acid residue of the fluorescent protein having the amino acid sequence shown in SEQ ID NO: 1 to histidine;

(2) substitution from an amino acid corresponding to 54th amino acid residue of the fluorescent protein having the amino acid sequence shown in SEQ ID NO: 1 to phenylalanine;

(3) substitution from an amino acid corresponding to 69th amino acid residue of the fluorescent protein having the amino acid sequence shown in SEQ ID NO: 1 to valine;

(4) substitution from an amino acid corresponding to 87th amino acid residue of the fluorescent protein having the amino acid sequence shown in SEQ ID NO: 1 to tyrosine;

(5) substitution from an amino acid corresponding to 93th amino acid residue of the fluorescent protein having the amino acid sequence shown in SEQ ID NO: 1 to methionine;

(6) substitution from an amino acid corresponding to 109th amino acid residue of the fluorescent protein having the amino acid sequence shown in SEQ ID NO: 1 to methionine;

(7) substitution from an amino acid corresponding to 121th amino acid residue of the fluorescent protein having the amino acid sequence shown in SEQ ID NO: 1 to isoleucine;

(8) substitution from an amino acid corresponding to 140th amino acid residue of the fluorescent protein having the amino acid sequence shown in SEQ ID NO: 1 to valine; or (9) substitution from an amino acid corresponding to 160th amino acid residue of the fluorescent protein having the amino acid sequence shown in SEQ ID NO: 1 to valine;

A further aspect of the present invention provides a method for producing a fluorescent protein capable of purple-to-blue photoconversion in response to irradiation with light, which comprises introducing at least one of the following amino acid substitutions in a fluorescent protein incapable of purple-to-blue photoconversion in response to irradiation with light:

(1) substitution from an amino acid corresponding to 60th amino acid residue of the fluorescent protein having the amino acid sequence shown in SEQ ID NO: 1 to alanine;

(2) substitution from an amino acid corresponding to 62th amino acid residue of the fluorescent protein having the amino acid sequence shown in SEQ ID NO: 1 to glycine;

(3) substitution from an amino acid corresponding to 63th amino acid residue of the fluorescent protein having the amino acid sequence shown in SEQ ID NO: 1 to histidine;

(4) substitution from an amino acid corresponding to 196th amino acid residue of the fluorescent protein having the amino acid sequence shown in SEQ ID NO: 1 to leucine; or (5) substitution from an amino acid corresponding to 198th amino acid residue of the fluorescent protein having the amino acid sequence shown in SEQ ID NO: 1 to threonine;

BRIEF DESCRIPTION OF THE DRAWINGS

FIG. 3 shows a comparison of amino acid sequences (SEQ ID NOS: 22, 23, 1, 12, 14, 16, 18, 20, respectively, in order of appearance), wherein *** represents chromophore-forming amino acids.

FIG. 5A left: before irradiation at 365 nm
FIG. 5A right: after irradiation at 365 nm
FIG. 5B: expression in HeLa cells
7 hours, 12 hours, and 18 hours after irradiation from the above
475AF20/530DF35 exp Isec Dichroic mirror 430DCLP
Xenon 75W, ND 10%T X10 UplanFI NA0.3

PREFERRED EMBODIMENTS OF THE INVENTION

Figure 1:
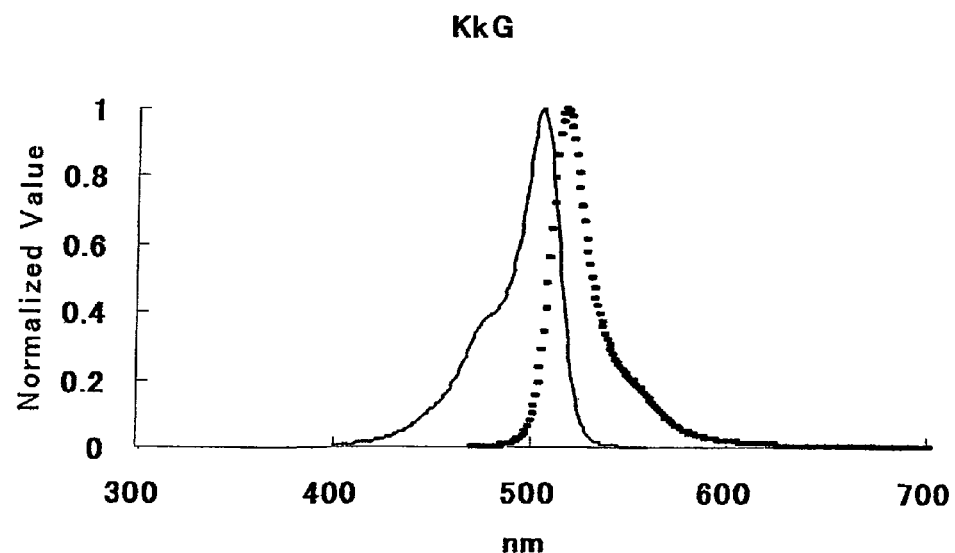
FIG. 1 shows the results of measuring the fluorescence emission spectrum and the excitation spectrum of the fluorescent protein (KkG) derived from *favia favus* of the present invention.

Hereafter, embodiments of the present invention are described in detail.

(1) Fluorescent Protein of the Present Invention

The fluorescent protein of the present invention is derived from *favia favus*, and has the following properties:
(1) an excitation maximum wavelength is 507 nm;
(2) a fluorescence maximum wavelength is 517 nm;
(3) a molar absorption coefficient at 482 nm is 80,000;
(4) a quantum yield is 0.68; and
(5) pH sensitivity of the fluorescence maximum is stable at pH 5 to pH 11.

*Favia favus* is one type of corals of the Cnidaria class, the Anthozoa class, the *Hexacorallia* subclass, and the Faviidae order.

The fluorescent protein of the present invention exhibits an excitation maximum wavelength of 507 nm and a fluorescence maximum wavelength of 517 nm as described in the following examples. The molar absorption coefficient at 482 nm is 80,000, and the quantum yield is 0.68. The molar absorption coefficient represents a quantity of absorbed photons per fluorescent molecule. The quantum yield is a numerical value indicating the quantity of absorbed photons that can be emitted as fluorescence.

Specific examples of the fluorescent protein of the present invention include those having any of the following amino acid sequences:
(a) an amino acid sequence shown in SEQ ID NO: 1; or
(b) an amino acid sequence comprising a deletion, substitution and/or addition of one or several amino acids with respect to the amino acid sequence shown in SEQ ID NO: 1, and having fluorescent properties.

The scope of "one or several" in the phrase "an amino acid sequence comprising a deletion, substitution and/or addition of one or several amino acids" used herein is not particularly limited in the present specification. For example, it means 1 to 20, preferably 1 to 10, more preferably 1 to 7, further preferably 1 to 5, and particularly preferably 1 to 3.

The term "having fluorescent properties" used herein covers all of the cases where any fluorescence is given. Various properties such as fluorescence intensity, excitation wavelength, fluorescence wavelength or pH sensitivity, may be changed or may remain unchanged, as compared with the protein having an amino acid sequence shown in SEQ ID NO: 1.

The method of obtaining the fluorescent protein of the present invention is not particularly limited. The protein may be either a protein synthesized by chemosynthesis, or recombinant protein produced by a gene recombination technique.

Where a recombinant protein is produced, it is necessary to obtain DNA encoding the protein. Appropriate primers are designed by using information regarding the amino acid sequence shown in SEQ ID NO: 1 of the sequence listing of the present specification and the nucleotide sequence shown in SEQ ID NO: 2. Using these primers, PCR is carried out by using cDNA library derived from *favia favus* as a template, so that DNA encoding the fluorescent protein of the present invention can be obtained. Where a partial fragment of DNA encoding the fluorescent protein of the present invention are obtained by the above-described PCR, the produced DNA fragments are ligated to one another by a gene recombination technique, so that DNA encoding the desired fluorescent protein can be obtained. The fluorescent protein of the present invention can be produced by introducing this DNA into an appropriate expression system. Expression in an expression system will be described later in the present specification.

(2) DNA of the Present Invention

According to the present invention, a gene encoding the fluorescent protein of the present invention is provided.

Specific example of DNA encoding the fluorescent protein of the present invention may include either one of the following DNA:

(a) DNA encoding the amino acid sequence shown in SEQ ID NO: 1; or (b) DNA encoding an amino acid sequence comprising a deletion, substitution and/or addition of one or several amino acids with respect to the amino acid sequence shown in SEQ ID NO: 1, and encoding a fluorescent protein.

Further example of DNA encoding the fluorescent protein of the present invention may include either one of the following DNA:

(a) DNA having a nucleotide sequence shown in SEQ ID NO: 2; or (b) DNA having a nucleotide sequence comprising a deletion, substitution and/or addition of one or several nucleotides with respect of the nucleotide sequence shown in SEQ ID NO: 2, and encoding a fluorescent protein.

The DNA of the present invention can be synthesized by, for example, the phosphoamidite method, or it can also be produced by polymerase chain reaction (PCR) using specific primers. The DNA of the present invention or a fragment thereof is produced by the method described above in the specification.

A method of introducing a desired mutation into a certain nucleic acid sequence is known to a person skilled in the art. For example, known techniques such as a site-directed mutagenesis, PCR using degenerated oligonucleotides, or the exposure of cells containing nucleic acid to mutagens or radioactive rays, are appropriately used, so as to construct DNA having a mutation. Such known techniques are described in, for example, Molecular Cloning: A Laboratory Manual, 2$^{nd}$ Ed., Cold Spring Harbor Laboratory, Cold Spring Harbor, N.Y., 1989; and Current Protocols in Molecular Biology, Supplements 1 to 38, John Wiley & Sons (1987-1997).

(3) Recombinant Vector of the Present Invention

The DNA of the present invention can be inserted into a suitable vector and used. The type of a vector used in the present invention is not particularly limited. For example, it may be either a vector that can autonomously replicate (e.g., a plasmid, etc.), or vector that is incorporated into the genomes of host cells when it is introduced into the host cells and is then replicated together with the chromosome into which it is incorporated.

The vector used in the present invention is preferably an expression vector. In an expression vector, elements necessary for transcription (e.g., a promoter, etc.) are functionally ligated to the DNA of the present invention. The promoter is a DNA sequence which shows a transcriptional activity in host cells, and it is appropriately selected depending on the type of host cells.

Examples of a promoter which can operate in bacterial cells may include a *Bacillus stearothermophilus* maltogenic amylase gene promoter, a *Bacillus licheniformis* alpha-amylase gene promoter, a *Bacillus amyloliquefaciens* BAN amylase gene promoter, a *Bacillus subtilis* alkaline protease gene promoter, a *Bacillus pumilus* xylosidase gene promoter, $P_R$ and $P_L$ promoters of phage rhamda, and lac, trp and tac promoters of *Escherichia coli*.

Examples of a promoter which can operate in mammalian cells may include an SV40 promoter, an MT-1 (metallothionein gene) promoter, and an adenovirus-2 major late promoter. Examples of a promoter which can operate in insect cells may include a polyhedrin promoter, a P10 promoter, an *Autographa californica* polyhedrosis basic protein promoter, a baculovirus immediate-early gene 1 promoter, and a baculovirus 39K delayed-early gene promoter. Examples of a promoter which can be operate in yeast host cells may include promoters derived from yeast glycolytic genes, an alcohol dehydrogenase gene promoter, a TPI1 promoter, and an ADH2-4c promoter.

Examples of a promoter which can operate in filamentous cells may include an ADH3 promoter and a tpiA promoter.

In addition, an appropriate terminator such as a human growth hormone terminator, or a TP11 terminator or ADH3 terminator for fungal cells, may be functionally bound to the DNA of the present invention, as necessary. The recombinant vector of the present invention may further have elements such as a polyadenylation signal (e.g., one derived from SV40 or the adenovirus 5E1b region), a transcription enhancer sequence (e.g., an SV40 enhancer), or a translation enhancer sequence (e.g., one encoding the adenovirus VA RNA).

The recombinant vector of the present invention may further comprise a DNA sequence which enables the replication of the recombinant vector in host cells. SV40 replication origin is an example of such a sequence (when the host cells are mammalian cells).

The recombinant vector of the present invention may further comprise a selective marker. Examples of such a selective marker may include genes, complements of which are absent from host cells, such as a dihydrofolate reductase (DHFR) gene or a *Shizosaccharomyces pombe* TPI gene, and drug resistant genes such as ampicillin, kanamycin, tetracycline, chloramphenicol, neomycin or hygromycin-resistant genes.

A method for ligating the DNA of the present invention, a promoter and, as desired, a terminator and/or a secretory signal sequence to one another and inserting these items into a suitable vector is known to a person skilled in the art.

(4) Transformant of the Present Invention

A transformant can be produced by introducing the DNA or recombinant vector of the present invention into a suitable host.

Any cell can be used as a host cell into which the DNA or recombinant vector of the present invention is introduced, as long as the DNA construct of the present invention can be expressed therein. Examples of such a cell may include bacteria, yeasts, fingal cells, and higher eukaryotic cells.

Examples of bacteria may include Gram-positive bacteria such as *Bacillus* or *Streptomyces*, and Gram-negative bacteria such as *Escherichia coli*. These bacteria may be transformed by the protoplast method or other known methods, using competent cells.

Examples of mammalian cells may include HEK 293 cells, HeLa cells, COS cells, BHK cells, CHL cells, and CHO cells. A method of transforming mammalian cells and expressing the introduced DNA sequence in the cells is also known. Examples of such a method may include the electroporation, the calcium phosphate method, and the lipofection method.

Examples of yeast cells may include those belonging to *Saccharomyces* or *Shizosaccharomyces*. Examples of such cells may include *Saccharomyces cerevisiae* and *Saccharomyces kluyveri*. Examples of a method of introducing a recombinant vector into yeast host cells may include the electroporation, the spheroplast method, and the lithium acetate method.

Examples of other fungal cells may include those belonging to Filamentous fungi such as *Aspergillus, Neurospora, Fusarium* or *Trichoderma*. Where Filamentous fungi are used as host cells, transformation can be carried out by incorporating DNA constructs into host chromosomes, so as to obtain recombinant host cells. Incorporation of DNA constructs into the host chromosomes is carried out by known methods, and such known methods may include homologous recombination and heterologous recombination.

Where insect cells are used as host cells, both a vector into which a recombinant gene is introduced and a baculovirus are co-introduced into insect cells, and a recombinant virus is obtained in the culture supernatant of the insect cells. Thereafter, insect cells are infected with the recombinant virus, so as to allow the cells to express proteins (described in, for example, Baculovirus Expression Vectors, A Laboratory Manual; and Current Protocols in Molecular Biology, Bio/Technology, 6, 47 (1988)).

The *Autographa californica* nuclear polyhedrosis virus, which is a virus infecting to insects belonging to *Barathra brassicae*, can be used as baculovirus.

Examples of insect cells used herein may include Sf9 and Sf21, which are *Spodoptera frugiperda* ovarian cells [Baculovirus Expression Vectors, A Laboratory Manual, W. H. Freeman & Company, New York, (1992)], and HiFive (manufactured by Invitrogen), which are *Trichoplusia ni* ovarian cells.

Examples of the method of co-introducing both a vector into which a recombinant gene has been introduced and the above baculovirus into insect cells to prepare a recombinant virus may include the calcium phosphate method and the lipofection method.

The above transformant is cultured in an appropriate nutritive medium under conditions enabling the introduced DNA construct to be expressed. In order to isolate and purify the fusion fluorescent protein of the present invention from the culture product of the transformant, common methods of isolating and purifying proteins may be used.

For example, where the protein of the present invention is expressed in a state dissolved in cells, after completion of the culture, cells are recovered by centrifugal separation, and the recovered cells are suspended in a water type buffer. Thereafter, the cells are disintegrated using an ultrasonic disintegrator or the like, so as to obtain a cell-free extract. A supernatant is obtained by centrifuging the cell-free extract, and then, a purified sample can be obtained from the supernatant by applying, singly or in combination, the following ordinary protein isolation and purification methods: the solvent extraction, the salting-out method using ammonium sulfate or the like, the desalting method, the precipitation method using an organic solvent, the anion exchange chromatography using resins such as diethylaminoethyl (DEAE) sepharose, the cation exchange chromatography using resins such as S-Sepharose FF (manufactured by Pharmacia), the hydrophobic chromatography using resins such as butyl sepharose or phenyl sepharose, the gel filtration method using a molecular sieve, the affinity chromatography, the chromatofocusing method, and the electrophoresis such as isoelectric focusing.

(5) Use of the Fluorescent Protein of the Present Invention and a Fusion Fluorescent Protein Comprising the Same The fluorescent protein of the present invention can be fused with another protein, so as to construct a fusion fluorescent protein.

A method of obtaining the fusion fluorescent protein of the present invention is not particularly limited. It may be either a protein synthesized by chemosynthesis, or recombinant protein produced by a gene recombination technique.

Where a recombinant protein is produced, it is necessary to obtain DNA encoding the protein. Appropriate primers are designed using the information regarding the amino acid sequence shown in SEQ ID NO: 1 of the sequence listing of the present specification and the nucleotide sequence shown in SEQ ID NO: 2 thereof. Using these primers, PCR is carried out using a DNA fragment containing the gene of the fluorescent protein of the present invention as a template, so as to produce DNA fragments necessary for construction of the DNA encoding the fluorescent protein of the present invention. Moreover, DNA fragments encoding a protein to be fused is also obtained in the same above manner.

Subsequently, the thus obtained DNA fragments are ligated to one another by a gene recombination technique, so that DNA encoding the desired fusion fluorescent protein can be obtained. This DNA is then introduced into an appropriate expression system, so that the fusion fluorescent protein of the present invention can be produced.

The fluorescent protein of the present invention has an extremely high utility value as a marker. This is to say, the fluorescent protein of the present invention is purified as a fusion protein with an amino acid sequence to be tested, and the fusion protein is introduced into cells by methods such as the microinjection. By observing the distribution of the fusion protein over time, targeting activity of the amino acid sequence to be tested can be detected in the cells.

The type of another protein (an amino acid sequence to be tested) with which the fluorescent protein of the present invention is fused is not particularly limited. Preferred examples may include proteins localizing in cells, proteins specific for intracellular organelles, and targeting signals (e.g., a nuclear transport signal, a mitochondrial presequence, etc.). In addition, the fluorescent protein of the present invention can be expressed in cells and used, as well as being introduced into cells by the microinjection or the like. In this case, a vector into which the DNA encoding the fluorescent protein of the present invention is inserted in such a way that it can be expressed, is introduced into host cells.

Moreover, the fluorescent protein of the present invention can also be used as a reporter protein to determine promoter activity. This is to say, a vector is constructed such that DNA encoding the fluorescent protein of the present invention is located downstream of a promoter to be tested, and the vector is then introduced into host cells. By detecting the fluorescence of the fluorescent protein of the present invention which is emitted from the cells, the activity of the promoter to be tested can be determined. The type of a promoter to be tested is not particularly limited, as long as it operates in host cells.

A vector used to detect the targeting activity of the above amino acid sequence to be tested or to determine promoter activity is not particularly limited. Examples of a vector preferably used for animal cells may include pNEO (P. Southern, and P. Berg (1982) J. Mol. Appl. Genet. 1: 327), pCAGGS (H. Niwa, K. Yamamura, and J. Miyazaki, Gene 108, 193-200 (1991)), pRc/CMV (manufactured by Invitrogen), and pCDM8 (manufactured by Invitrogen). Examples of a vector preferably used for yeasts may include pRS303, pRS304, pRS305, pRS306, pRS313, pRS314, pRS315, pRS316 (R. S. Sikorski and P. Hieter (1989) Genetics 122: 19-27), pRS423, pRS424, pRS425, pRS426 (T. W. Christianson, R. S. Sikorski, M. Dante, J. H. Shero, and P. Hieter (1992) Gene 110: 119-122).

In addition, the type of cells used herein is also not particularly limited. Various types of animal cells such as L cells, BalbC-3T3 cells, NIH3T3 cells, CHO (Chinese hamster ovary) cells, HeLa cells or NRK (normal rat kidney) cells, yeast cells such as *Saccharomyces cerevisiae, Escherichia coli* cells, or the like can be used. Vector can be introduced into host cells by common methods such as the calcium phosphate method or the electroporation.

The above obtained fusion fluorescent protein of the present invention wherein the fluorescent protein of the present invention is fused with another protein (referred to as a protein X) is allowed to be expressed in cells. By monitoring a fluorescence emitted, it becomes possible to analyze the localization or dynamics of the protein X in cells. That is, cells transformed or transfected with DNA encoding the fusion fluorescent protein of the present invention are observed with a fluorescence microscope, so that the localization and dynamics of the protein X in the cells can be visualized and thus analyzed.

For example, by using a protein specific for an intracellular organella as a protein X, the distribution and movement of a nucleus, a mitochondria, an endoplasmic reticulum, a Golgi body, a secretory vesicle, a peroxisome, etc., can be observed.

Moreover, for example, axis cylinders or dendrites of the nerve cells show an extremely complicated change in strikes in an individual who is under development. Accordingly, fluorescent labeling of these sites enables a dynamic analysis.

The fluorescence of the fluorescent protein of the present invention can be detected with a viable cell. Such detection can be carried out using, for example, a fluorescence microscope (Axiophoto Filter Set 09 manufactured by Carl Zeiss) or an image analyzer (Digital Image Analyzer manufactured by ATTO).

The type of a microscope can be appropriately selected depending on purposes. Where frequent observation such as pursuit of a change over time is carried out, an ordinary incident-light fluorescence microscope is preferable. Where observation is carried out while resolution is emphasized, for example, in the case of searching localization in cells specifically, a confocal laser scanning microscope is preferable. In terms of maintenance of the physiological state of cells and prevention from contamination, an inverted microscope is preferable as a microscope system. When an erecting microscope with a high-powered lens is used, a water immersion lens can be used.

A filter set can be appropriately selected depending on the fluorescence wavelength of a fluorescent protein. In the case of the fluorescent protein of the present invention, a filter having an excitation light between approximately 490 and 510 nm and a fluorescence between approximately 510 and 530 nm can be preferably used.

When viable cells are observed over time using a fluorescence microscope, a high sensitive cooled CCD camera is used, since photography is carried out in a short time. In the case of the cooled CCD camera, CCD is cooled to decrease thermal noise, so that a weak fluorescence image can be clearly photographed by exposure in a short time.

(6) Kit of the Present Invention

The present invention provides a kit for analyzing the localization of intracellular components and/or analyzing physiologically active substances, which is characterized in that it comprises at least one selected from the fluorescent protein, the fusion fluorescent protein, the DNA, the recombinant vector, or the transformant, which are described in the present specification. The kit of the present invention can be produced from commonly used materials that are known per se, by using common methods.

Reagents such as the fluorescent protein or the DNA are dissolved in an appropriate solvent, so that the reagents can be prepared in a form suitable for conservation. Water, ethanol, various types of buffer solution, etc. can be used as such a solvent.

The present invention will be further described in the following examples. However, the present invention is not limited by these examples.

EXAMPLES

Example 1

Isolation of Novel Fluorescent Protein Gene from Coral (Faviidae)

(1) Extraction of Total RNA

The fluorescent protein gene was isolated from fluorescing corals. *Favia favus* was employed as a material. Faviidae was crushed with a hammer, 15 ml of TRIzol (GIBCO BRL) was added to 11 g (a wet weight) of the crushed Faviidae, and the resultant was agitated, followed by centrifugation at 1,500×g for 10 minutes. Chloroform (3 ml) was added to the supernatant, and the mixture was agitated for 15 seconds, allowed to stand for 3 minutes, and then centrifuged at 7,500×g for 15 minutes. Isopropanol (3.75 ml) was added to the supernatant, and the mixture was agitated for 15 seconds, allowed to stand for 10 minutes, and then centrifuged at 17,000×g for 10 minutes. The supernatant was discarded, 6 ml of 70% ethanol was added, and the mixture was centrifuged at 17,000×g for 10 minutes. The supernatant was discarded, and the precipitate was dissolved in 200 µl of DEPC water. The total RNA dissolved in DEPC water was diluted 100-fold, and OD260 and OD280 thereof were measured to determine the RNA concentration. 20 µg of total RNA was obtained.

(2) Synthesis of First Strand cDNA cDNA (33 µl) was synthesized from 3 µg of total RNA using a First-strand cDNA synthesis kit "Ready-To-Go" (Amersham Pharmacia).

(3) Degenerated PCR

From 33 µl of the synthesized first strand cDNA, 3 µl thereof was separated, and PCR was carried out using the same as a template. The amino acid sequences of existing fluorescent proteins were analyzed, similar portions were extracted, the extracted sequences were converted into nucleotide sequences, and primers were designed based thereon.
Primers used:

```
                                              (SEQ ID NO: 3)
    5'-GGI WSB GTI AAY GGV CAY DAN TT -3'
    (Primer 1)

(SEQ ID NO: 4)
    5'-AACTGGAAGAATTCGCGGCCGCAGGAA -3'
    (Primer 2)
R = A or G, Y = C or T, V = A, C, or G, D = A, G or T
```

| Composition of PCR solution | |
|---|---|
| Template (first strand cDNA) | 3 μl |
| ×10 taq buffer | 5 μl |
| 2.5 mM dNTPs | 4 μl |
| 100 μM primer 1 | 1 μl |
| 100 μM primer 2 | 1 μl |
| MilliQ | 35 μl |
| Taq polymerase (5 U/μl) | 1 μl |
| PCR conditions | |
| 94° C. for 1 min (PAD) | |
| 94° C. for 30 sec (denaturation) | |
| 52° C. for 30 sec (annealing of primer to template) | |
| 72° C. for 1 min (primer elongation) | |
| 72° C. for 7 min (final elongation) | |
| 4° C. (preservation) | |

The amplification product (1 μl) obtained in the first PCR cycle was used as a template to carry out PCR under the same temperature conditions, provided that the following primers were used:

```
                                              (SEQ ID NO: 5)
5'-TGC CWT TTG CIT TIG AYA TIT TG -3'
(Primer 3)

(SEQ ID NO: 6)
5'-GTC ITC TTY TGC ACI ACI GGI CCA TYD GVA GGA

AA -3'
(Primer 4)
```

A band of an expected size of 350 bp was cleaved via agarose gel electrophoresis and then purified.
(4) Subcloning and Nucleotide Sequencing
The purified DNA fragment was ligated to the pT7-Blue vector (Novagen). The resultant was transformed into the E. coli strain (TG1) for blue/white selection, plasmid DNA was purified from E. coli white colonies, and the nucleotide sequence of the inserted DNA fragment was determined using a DNA sequencer. The determined nucleotide sequences were compared with the nucleotide sequences of other fluorescent protein genes to determine whether or not the nucleotide sequence of the DNA of interest was derived from a fluorescent protein. As to the nucleotide sequences that had been determined to be a part of a fluorescent protein gene, cloning of a full-length gene was carried out by the 5'-RACE method and by the 3'-RACE method.
(5) 5'-RACE Method
In order to determine the nucleotide sequence on the 5'-side of the DNA fragment obtained via degenerated PCR, the 5'-RACE method was implemented using the 5'-RACE System for Rapid Amplification of cDNA Ends, Version 2.0 (GIBCO BRL). The total RNA (3 μg) prepared in (1) was used as a template.

The following primers were used for the first amplification of DC-tailed cDNA.

```
                                              (SEQ ID NO: 7)
5'-GGCCACGCGTCGACTAGTACGGGIIGGGIIGGGIIG-3'
(Primer 5)

(SEQ ID NO: 8)
5'-TTG TCA AGA TAT CGA AAG CGA ACG GCA GAG -3'
(Primer 6)
I = inosine
```

The following primers were used for the second amplification.

```
                                              (SEQ ID NO: 9)
    5'-GGCCACGCGTCGACTAGTAC-3'

(SEQ ID NO: 10)
    5'-GTC CAC CCT CTA CGA CTT TGA GTT CCA TAT-3'
```

PCR conditions were set in accordance with the protocol included in the kit.
The amplified 700-bp band was cleaved via agarose gel electrophoresis and then purified. The purified DNA fragment was ligated to the pT7-Blue vector (Novagen). The resultant was transformed into the E. coli strain (TG1) for blue/white selection, plasmid DNA was purified from E. coli white colonies, and the nucleotide sequence of the inserted DNA fragment was determined using a DNA sequencer.
(6) Determination of Full Length Nucleotide Sequences and Protein Expression in E. coli
A primer was prepared from a portion corresponding to the N-terminus of the protein obtained in (5), an oligo dT primer was used for the C-terminus, and PCR was carried out using the first strand cDNA prepared in (2) as a template.
Primer used:

```
                                              (SEQ ID NO: 11)
5'-CCC GGA TCC GAT GAG TGT GAT TAC AWC AGA AAT GAA

GAT GGA GC-3'
(Primer 7)
```

| Composition of PCR solution | |
|---|---|
| Template (first strand cDNA) | 3 μl |
| ×10 pyrobest buffer | 5 μl |
| 2.5 mM dNTPs | 4 μl |
| 100 μM primer 7 | 1 μl |
| 100 μM oligo dT primer | 1 μl |
| MilliQ | 35 μl |
| Pyrobest polymerase (5 U/μl) | 1 μl |
| PCR conditions | |
| 94° C. for 1 min (PAD) | |
| 94° C. for 30 sec (denaturation) | |
| 52° C. for 30 sec (annealing of primer to template) | |
| 72° C. for 1 min (primer elongation) | |
| The above 3 steps were repeated 30 times. | |
| 72° C. for 7 min (final elongation) | |
| 4° C. (preservation) | |

The amplified band of approximately 900 bp was cleaved via agarose gel electrophoresis, purified, subcloned into the BamHI/EcoRI site of the pRSET vector (Invitrogen), and then expressed in the E. coli strain (JM109-DE3). The plasmid was recovered, and the inserted full length nucleotide sequence was determined. The clone was designated as KkG.

The full-length nucleotide sequence is shown in SEQ ID NO: 2, and the full-length amino acid sequence is shown in SEQ ID NO: 1.

Since the expressed protein was constructed to have a His-tag at its N-terminus, the expressed protein was purified on Ni-Agarose gel (QIAGEN). Purification was carried out in accordance with the protocol included in the kit. Subsequently, the properties of the purified protein were analyzed.

(7) Analysis of Fluorescence Properties

The absorption spectrum was measured using a solution of 10 μM fluorescent protein (KkG) in PBS. The molar absorption coefficient was determined based on the peak value of this spectrum. The absorption peak was observed at 507 nm, the fluorescent protein was diluted with the aforementioned buffer to adjust the absorption at 450 nm to 0.005, and the fluorescence emission spectra after excitation at 450 nm were measured (FIG. 1). Similarly, the fluorescence emission spectrum of EGFP (CLONTECH) was measured in a state where the absorption at 450 nm is 0.005. The quantum yield of EGFP was set at 0.6, and the quantum yield of the protein of the present invention was determined. The results are shown in Table 1.

TABLE 1

| | Excitation maximum | Fluorescence maximum | Molar absorption coefficient | Quantum yield | pH sensitivity | Amino acid number |
|---|---|---|---|---|---|---|
| KkG | 507 nm | 517 nm | 80,000 (482 nm) | 0.68 | Stable at pH 5 to 11 | 227 |

(8) Measurement of pH Sensitivity

The fluorescent protein of the present invention was diluted with the following buffers, and the fluorescence emission spectra were measured.

Figure 2:
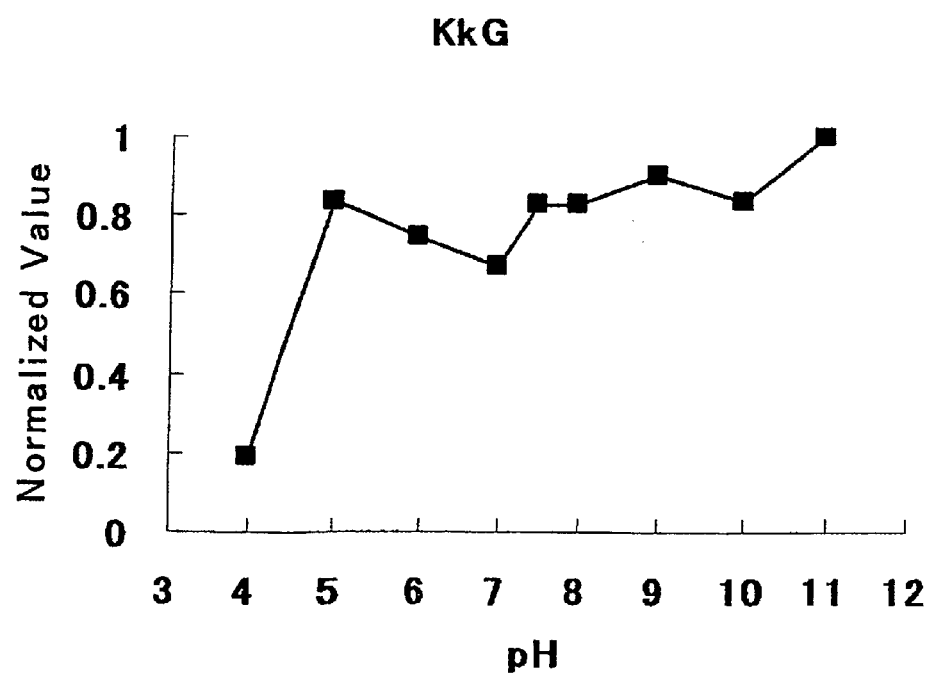
FIG. 2 shows the pH dependence of the fluorescent protein (KkG) derived from *favia favus* of the present invention.

The pH levels of the buffers are as follows.
pH4, 5: Acetate buffer
pH6: MES buffer
pH7: MOPS buffer
pH8: HEPES buffer
pH9, 10: Glycine buffer
pH11: Phosphate buffer The results of pH dependence measured at the fluorescence maximum wavelength are shown in FIG. 2.

Example 2

Preparation of Various Fluorescent Proteins with Improved Fluorescence Properties (1) Preparation of Fluorescent Protein Capable of Green-to-red Photoconversion in Response to Irradiation with Light (Ultraviolet Rays and Purple Light)

Figure 3:
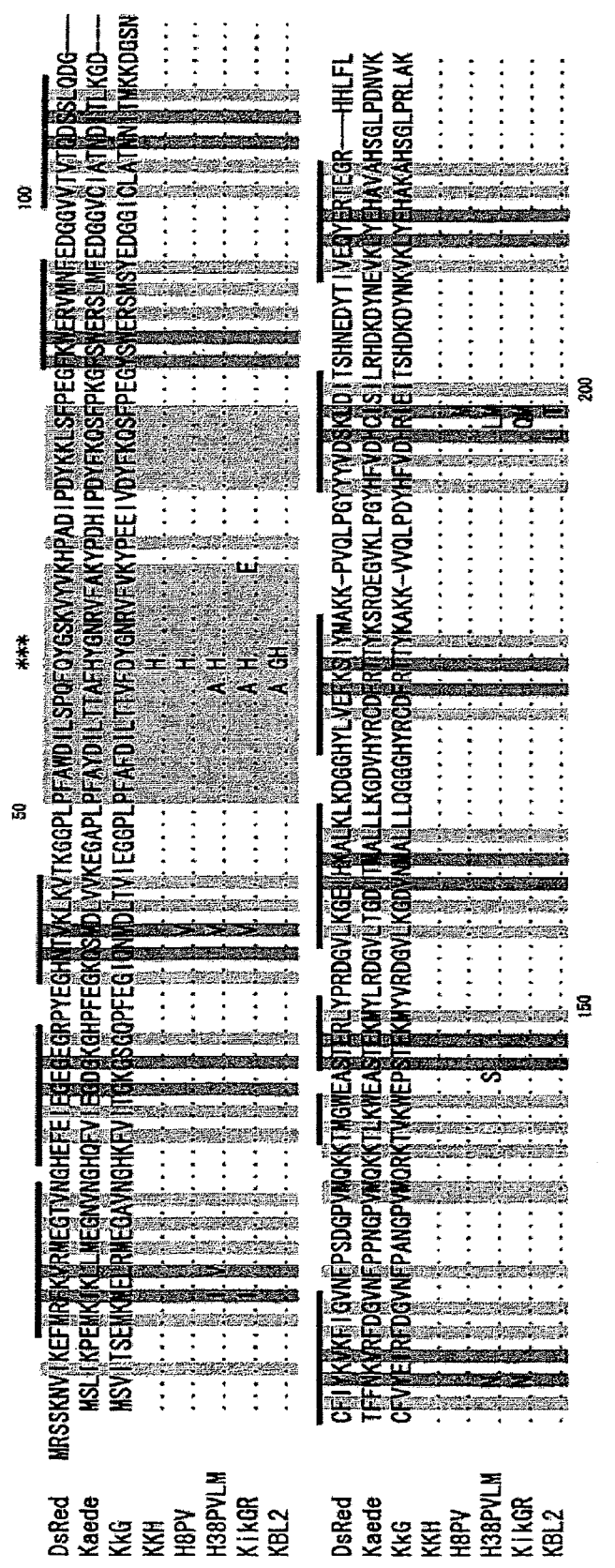
Figure 4:
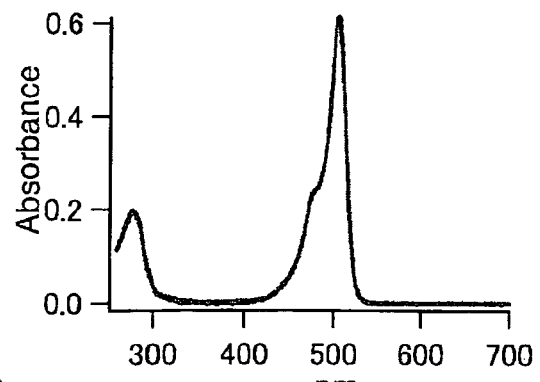
FIG. 4 shows changes in spectral properties via light irradiation at 365 nm.
A1: the absorption spectra of KkG
A2: the absorption spectra of KKH after irradiation with light
A3: changes in the absorption spectra of KikGR via irradiation with light
A4: changes in the excitation spectra and in the fluorescence emission spectra of KikGR via irradiation with light
Figure 4:
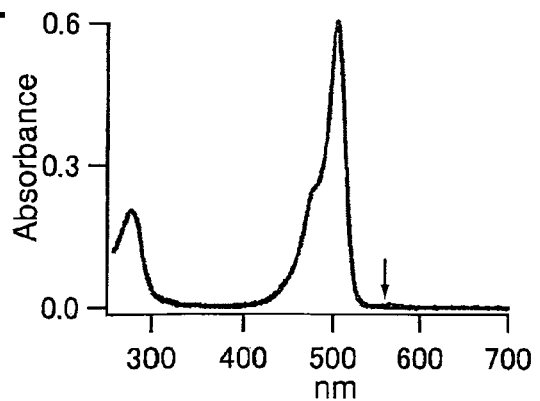
Figure 4:
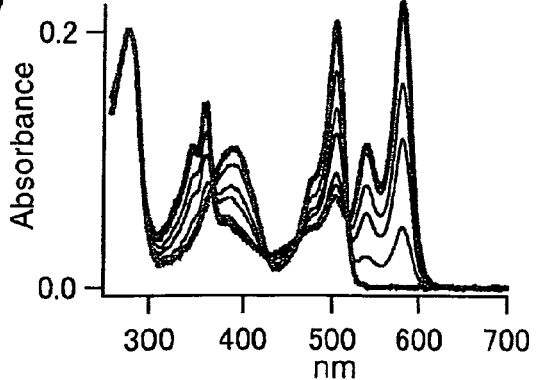
Figure 4:
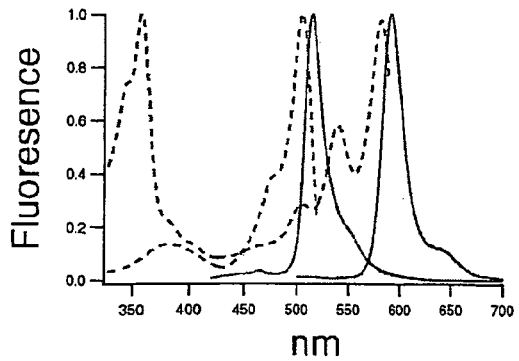

By substitution from aspartic acid (D) to histidine (H) at 62th amino acid residue of the fluorescent protein KkG that is incapable of green-to-red photoconversion in response to irradiation with light, the properties of this protein could be modified so that it became capable of green-to-red photoconversion in response to irradiation with light (where the resulting protein is referred to as "KKH," the amino acid sequence of which is shown in SEQ ID NO: 12, and the nucleotide sequence of which is shown in SEQ ID NO: 13) (FIGS. 3 and 4). In FIG. 4A2, an arrow indicates an increase in the absorption (583 nm) at a portion that emits red fluorescence upon irradiation with light. By substitution from methionine (M) to valine (V) at 40th amino acid residue, substitution from aspartic acid (D) to histidine (H) at 62th amino acid residue, and substitution from isoleucine (I) to methionine (M) at 198th amino acid residue in the fluorescent protein KkG, a fluorescent protein having photosensitivity higher than that of the fluorescent protein (KKH) that is capable of green-to-red photoconversion in response to irradiation with light, i.e., a fluorescent protein capable of green-to-red photoconversion with a weak light (H8PV, the amino acid sequence of which is shown in SEQ ID NO: 14, and the nucleotide sequence of which is shown in SEQ ID NO: 15), could be obtained (FIG. 3).

By substitution from methionine (M) to isoleucine (I) at 10th amino acid residue, substitution from leucine (L) to valine (V) at 12th amino acid residue, substitution from methionine (M) to valine (V) at 40th amino acid residue, substitution from valine (V) to alanine (A) at 60th amino acid residue, substitution from aspartic acid (D) to histidine (H) at 62th amino acid residue, substitution from tyrosine (Y) to asparagine (N) at 119th amino acid residue, substitution from proline (P) to serine (S) at 144th amino acid residue, substitution from arginine (R) to leucine (L) at 197th amino acid residue, and substitution from isoleucine (I) to methionine (M) at 198th amino acid residue in the fluorescent protein KkG, a fluorescent protein having photosensitivity higher than that of the fluorescent protein (H8PV) capable of green-to-red photoconversion in response to irradiation with light, i.e., a fluorescent protein capable of green-to-red photoconversion with a weak light (H38PVLM, the amino acid sequence of which is shown in SEQ ID NO: 16, and the nucleotide sequence of which is shown in SEQ ID NO: 17), could be obtained (FIG. 3).

By substitution from methionine (M) to isoleucine (I) at 10th amino acid residue, substitution from methionine (M) to valine (V) at 40th amino acid residue, substitution from valine (V) to alanine (A) at 60th amino acid residue, substitution from aspartic acid (D) to histidine (H) at 62th amino acid residue, substitution from lysine (K) to glutamic acid (E) at 70th amino acid residue, substitution from tyrosine (Y) to asparagine (N) at 119th amino acid residue, substitution from arginine (R) to glutamine (Q) at 197th amino acid residue, and substitution from isoleucine (I) to methionine (M) at 198th amino acid residue in the fluorescent protein KkG, a fluorescent protein having photosensitivity higher than that of the fluorescent protein (H38PVLM) capable of green-to-red photoconversion in response to irradiation with light, i.e., a fluorescent protein capable of green-to-red photoconversion with a weak light (KikGR, the amino acid sequence of which is shown in SEQ ID NO: 18, and the nucleotide sequence of which is shown in SEQ ID NO: 19), could be obtained (FIGS. 3 and 4).

FIG. 4A3 and FIG. 4A4 show that absorption (507 nm) at a portion emitting green fluorescence (517 nm) is gradually decreased upon irradiation with light and absorption (583 nm) at a portion emitting red fluorescence (593 nm) is gradually increased. That is, a fluorescent protein capable of green-to-red photoconversion in response to irradiation with light can be produced by introducing substitution from an amino acid corresponding to 62th amino acid residue of KkG (more specifically, this amino acid refers to X of 3 amino acid residues XYG which forms the chromophore shown in an asterisk portion of FIG. 3, wherein X represents any amino acid, Y generally represents tyrosine and optionally an aromatic amino acid such as phenylalanine, tryptophan, or histidine, and G represents glycine) to histidine in a fluorescent protein KkG incapable of green-to-red photoconversion in response to irradiation with light. Further, when any fluorescent protein incapable of green-to-red photoconversion in response to irradiation with light which has substitution from an amino acid corresponding to 62th amino acid residue of KkG to histidine (H) further comprises any of the following amino acid substitutions; namely, substitution from an amino acid corresponding to 10th amino acid residue of KkG to isoleucine (I), substitution from an amino acid corresponding to 12th amino acid residue of KkG to valine (V), substitution from an amino acid corresponding to 40th amino acid residue of KkG to valine (V), substitution from an amino acid corresponding to 60th amino acid residue of KkG to alanine (A), substitution from an amino acid corresponding to 70th amino acid residue of KkG to glutamic acid (E), substitution from an amino acid corresponding to 119th amino acid residue of KkG to asparagine (N), substitution from an amino acid corresponding to 144 amino acid residue of KkG to serine (S), substitution from an amino acid corresponding to 197th amino acid residue of KkG to leucine (L) or glutamine (Q), or substitution from an amino acid corresponding to 198th amino acid residue of KkG to methionine (M); a fluorescent protein capable of green-to-red photoconversion in response to irradiation with light can be prepared, and a fluorescent protein with high photosensitivity, i.e., a fluorescent protein capable of green-to-red photoconversion with a weak light, can be obtained.

Figure 5:
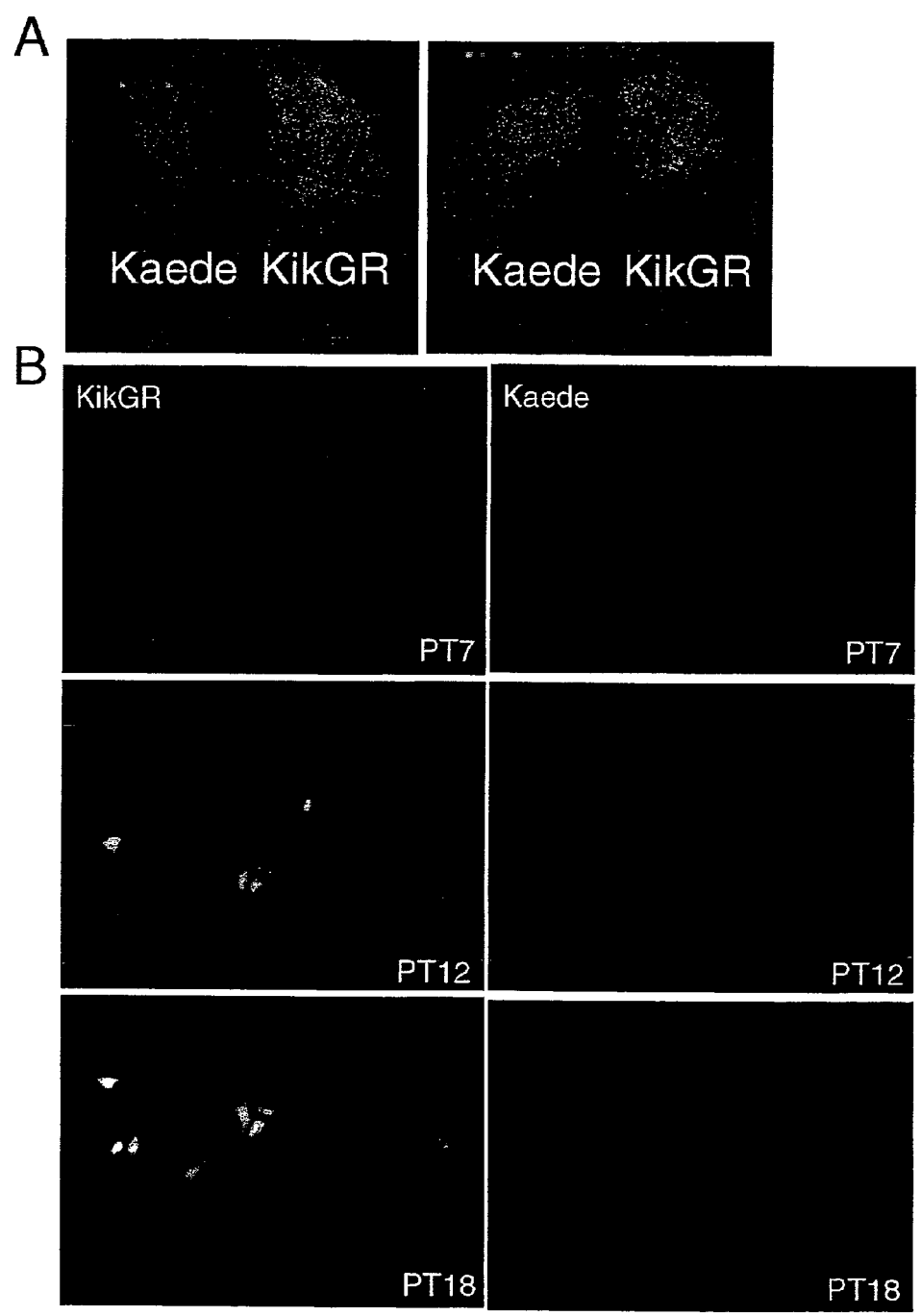
FIG. 5 shows a comparison of fluorescence intensities in *E. coli* and in HeLa cells.
Figure 6:
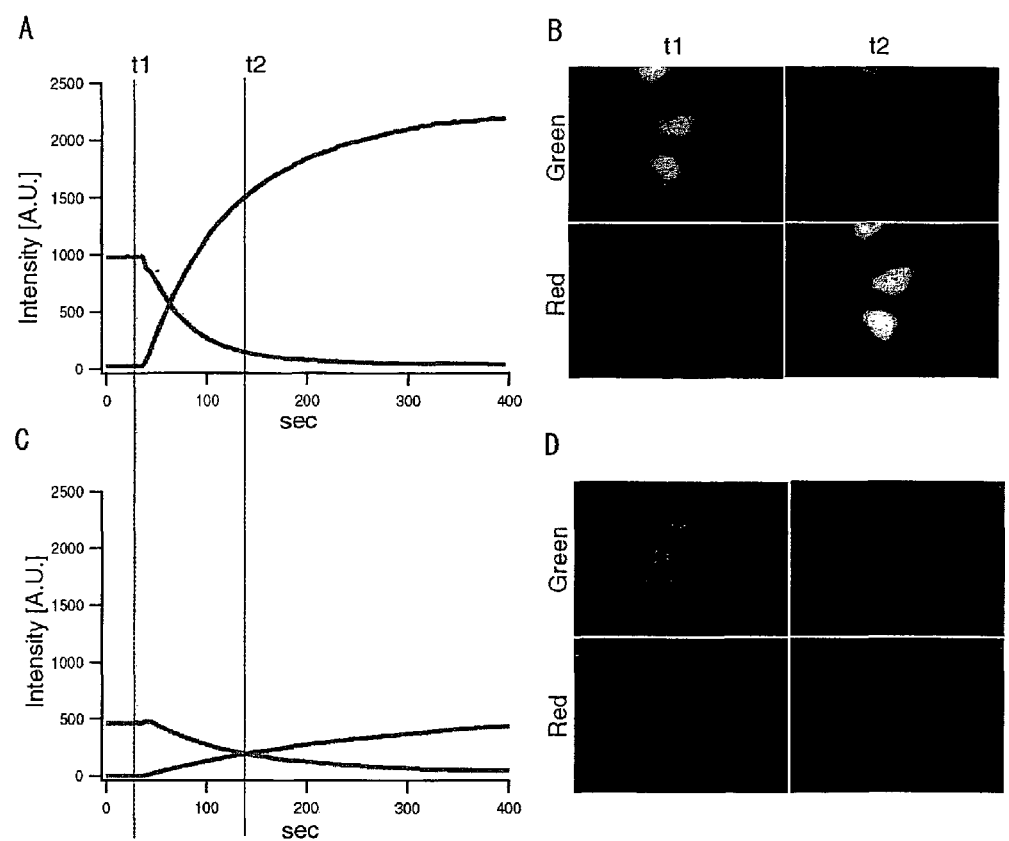
FIG. 6 shows green-to-red photoconversion and comparison of brightness (A: change in KikGR fluorescence intensities; B: an image of KikGR-expressing cells; C: change in Kaede fluorescence intensities; and D: an image of Kaede-expressing cells).
Green 475AF20/530DF35 exp 50 ms
Red 550DF30/575ALP exp 100 ms
Violet 400DF 10 exp 100 ms
Dicroic mirror: 430DCLP
Xenon75W ND10% T
Bin4 Cool SNAP HQ
X40 UApo340/NA1.35
Figure 7:
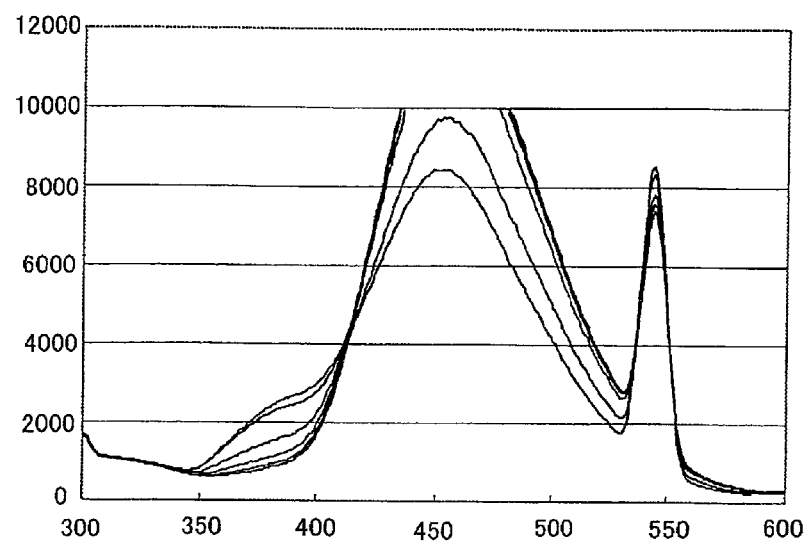
FIG. 7 shows changes in the fluorescence emission spectra of KBL2 via ultraviolet irradiation at 270 nm (including the second-order light from the grating), wherein fluorescence at 380 nm is decreased and fluorescence at 450 nm is increased upon ultraviolet irradiation.
Figure 8:
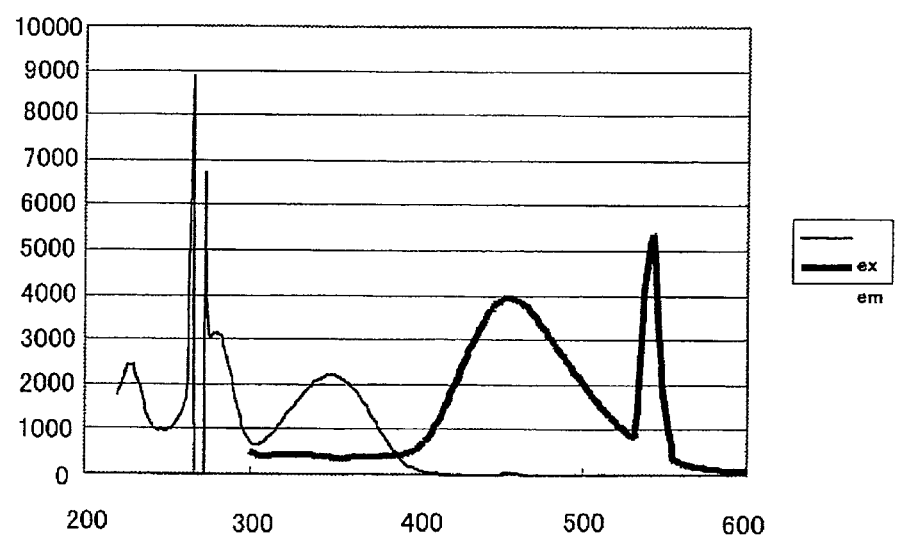
FIG. 8 shows the excitation spectra and the fluorescence emission spectra of KBL2 after photoconversion (including the second-order light from the grating).
Figure 9:
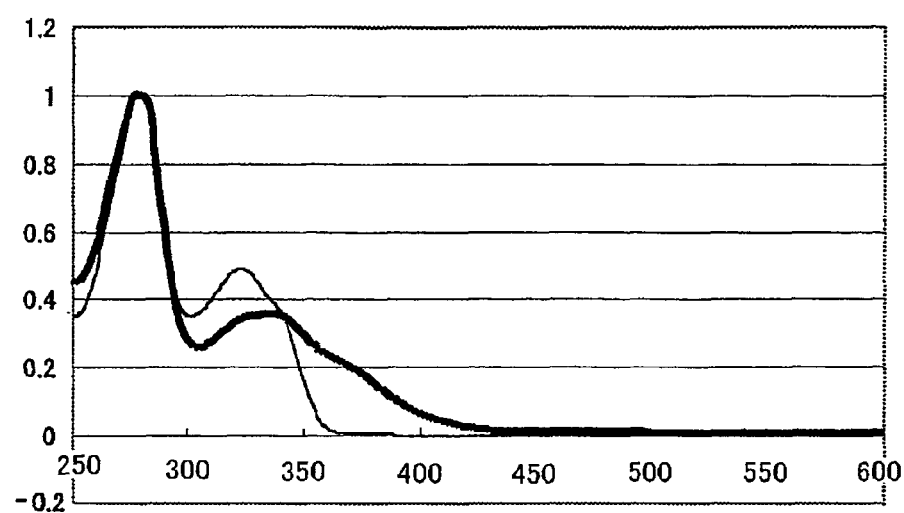
FIG. 9 shows changes in the absorption spectra via irradiation at 365 nm (fine line: before irradiation; bold line: after irradiation).

The fluorescent proteins Kaede and KikGR capable of green-to-red photoconversion in response to irradiation with light were expressed in E. coli and then compared. As a result, the fluorescence intensity of KikGR was found to be higher than that of Kaede both before and after photoconversion (FIG. 5A). When the Kaede and KikGR genes were introduced into the HeLa cells and expressed therein, KikGR emitted fluorescence earlier than Kaede (FIG. 5B). When KikGR and Kaede that had been expressed in the HeLa cells were irradiated with light to result in green-to-red photoconversion in the cells, the rate of green-to-red photoconversion of KikGR was apparently faster than that of Kaede, and the fluorescence intensity of KikGR was stronger (FIGS. 6A, 6B, 6C, and 6D). Accordingly, it is easily expected that the rate of green-to-red photoconversion can be increased and the fluorescence intensity can be enhanced by introducing the same amino acid substitution as that of the case of KikGR at a portion of Kaede which was found to be different from that of KikGR upon comparison of amino acid sequences. In particular, the shaded portion in FIG. 3 is considered to significantly affect fluorescence properties, since the amino acid side chain is directed inside the protein when the protein has a three-dimensional structure. Specifically, when any fluorescent protein having substitution from an amino acid corresponding to 62th amino acid residue of KkG to histidine (H) comprises any of the following amino acid substitutions; namely substitution from an amino acid corresponding to 54th amino acid residue of KkG to phenylalanine (F), substitution from an amino acid corresponding to 69th amino acid residue of KkG to valine (V), substitution from an amino acid corresponding to 87th amino acid residue of KkG to tyrosine (Y), substitution from an amino acid corresponding to 93th amino acid residue of KkG to methionine (M), substitution from an amino acid corresponding to 109th amino acid residue of KkG to methionine (M), substitution from an amino acid corresponding to 121th amino acid residue of KkG to isoleucine (I), substitution from an amino acid corresponding to 140th amino acid residue of KkG to valine (V), or substitution from an amino acid corresponding to 160th amino acid residue of KkG to valine (V); a fluorescent protein with an increased rate of green-to-red photoconversion and enhanced fluorescence intensity can be produced.

(2) Preparation of Fluorescent Protein Capable of Purple-to-blue Photoconversion in Response to Irradiation with Light (Ultraviolet Rays and Purple Light)

The fluorescent protein KkG incapable of purple-to-blue photoconversion in response to irradiation with light was subjected to substitution from valine (V) to alanine (A) at 60th amino acid residue, substitution from aspartic acid (D) to glycine (G) at 62th amino acid residue, substitution from tyrosine (Y) to histidine (H) at 63th amino acid residue, substitution from histidine (H) to leucine (L) at 197th amino acid residue, and substitution from isoleucine (I) to threonine (T) at 199th amino acid residue. Thus, the properties of this protein could be modified so that it became capable of purple (380 nm)-to-blue (450 nm) photoconversion in response to irradiation with light (where the resulting protein is referred to as "Kbl2," the amino acid sequence of which is shown in SEQ ID NO: 20, and the nucleotide sequence of which is shown in SEQ ID NO: 21) (FIGS. 3, 7, 8 and 9). Specifically, a fluorescent protein capable of purple-to-blue photoconversion in response to irradiation with light can be prepared by introducing all or any one of the following substitutions in any fluorescent protein; substitution from an amino acid corresponding to 60th amino acid residue of KkG to alanine (A), substitution from an amino acid corresponding to 62th amino acid residue of KkG to glycine (G), substitution from an amino acid corresponding to 63th amino acid residue of KkG to histidine (H), substitution from an amino acid corresponding to 196th amino acid residue of KkG to leucine (L), and substitution from an amino acid corresponding to 198th amino acid residue of KkG to threonine (T).

Industrial Applicability

The present invention provides a novel fluorescent protein derived from *favia favus*. The fluorescent protein of the present invention is a novel protein having primary structures that differ from those of existing fluorescent proteins. The fluorescent protein of the present invention has given fluorescence properties and thus is useful in molecular biological analysis. Therefore, use of the fluorescent protein of the present invention enables fluorescence labeling of mammalian cells without causing toxicity. Use of a novel gene that is discovered through the present invention as a starting material enables provision of fluorescent substances exhibiting a wide variety of properties.

The invention claimed is:

1. An isolated DNA comprising any of the following nucleotide sequences:

(a) the nucleotide sequence shown in SEQ ID NO: 2, 13, 15, 17, 19, or 21; or (b) the nucleotide sequence of SEQ ID NO: 2 with 1 to 60 nucleotide substitutions, and encoding a fluorescent protein.

2. A recombinant vector having the DNA of claim 1.

3. A transformant having the DNA of claim 1.

* * * * *

SEQUENCE LISTING

<160> NUMBER OF SEQ ID NOS: 23

<210> SEQ ID NO 1
<211> LENGTH: 227
<212> TYPE: PRT
<213> ORGANISM: Favia favus

<400> SEQUENCE: 1

```
Met Ser Val Ile Thr Ser Glu Met Lys Met Glu Leu Arg Met Glu Gly
1               5                   10                  15

Ala Val Asn Gly His Lys Phe Val Ile Thr Gly Lys Gly Ser Gly Gln
            20                  25                  30

Pro Phe Glu Gly Ile Gln Asn Met Asp Leu Thr Val Ile Glu Gly Gly
        35                  40                  45

Pro Leu Pro Phe Ala Phe Asp Ile Leu Thr Thr Val Phe Asp Tyr Gly
50                  55                  60

Asn Arg Val Phe Val Lys Tyr Pro Glu Glu Ile Val Asp Tyr Phe Lys
65                  70                  75                  80

Gln Ser Phe Pro Glu Gly Tyr Ser Trp Glu Arg Ser Met Ser Tyr Glu
            85                  90                  95

Asp Gly Gly Ile Cys Leu Ala Thr Asn Asn Ile Thr Met Lys Lys Asp
        100                 105                 110

Gly Ser Asn Cys Phe Val Tyr Glu Ile Arg Phe Asp Gly Val Asn Phe
    115                 120                 125

Pro Ala Asn Gly Pro Val Met Gln Arg Lys Thr Val Lys Trp Glu Pro
130                 135                 140

Ser Thr Glu Lys Met Tyr Val Arg Asp Gly Val Leu Lys Gly Asp Val
145                 150                 155                 160

Asn Met Ala Leu Leu Leu Gln Gly Gly His Tyr Arg Cys Asp Phe
            165                 170                 175

Arg Thr Thr Tyr Lys Ala Lys Lys Val Val Gln Leu Pro Asp Tyr His
        180                 185                 190

Phe Val Asp His Arg Ile Glu Ile Thr Ser His Asp Lys Asp Tyr Asn
    195                 200                 205

Lys Val Lys Leu Tyr Glu His Ala Lys Ala His Ser Gly Leu Pro Arg
210                 215                 220

Leu Ala Lys
225
```

<210> SEQ ID NO 2
<211> LENGTH: 684
<212> TYPE: DNA
<213> ORGANISM: Favia favus
<220> FEATURE:
<221> NAME/KEY: CDS
<222> LOCATION: (1)..(681)

<400> SEQUENCE: 2

```
atg agt gtg att aca tca gaa atg aag atg gag ctg cgt atg gaa ggc    48
Met Ser Val Ile Thr Ser Glu Met Lys Met Glu Leu Arg Met Glu Gly
1               5                   10                  15 gct gta aac ggg cac aag ttc gtg att aca ggg aaa gga agt ggc cag    96
Ala Val Asn Gly His Lys Phe Val Ile Thr Gly Lys Gly Ser Gly Gln
            20                  25                  30 cct ttc gag gga ata cag aat atg gac ctg aca gtc ata gag ggc gga   144
Pro Phe Glu Gly Ile Gln Asn Met Asp Leu Thr Val Ile Glu Gly Gly
        35                  40                  45 cct ctt cct ttt gct ttc gat atc ctg aca aca gta ttc gat tac ggc   192
Pro Leu Pro Phe Ala Phe Asp Ile Leu Thr Thr Val Phe Asp Tyr Gly
50                  55                  60 aac cgg gta ttt gtc aaa tac cca gaa gaa ata gta gac tac ttc aag   240
Asn Arg Val Phe Val Lys Tyr Pro Glu Glu Ile Val Asp Tyr Phe Lys
65                  70                  75                  80 cag tcg ttt cct gag ggt tat tct tgg gaa cga agc atg agt tac gaa   288
Gln Ser Phe Pro Glu Gly Tyr Ser Trp Glu Arg Ser Met Ser Tyr Glu
```

```
gac ggg gga att tgc ctc gcc aca aac aat ata acg atg aag aaa gac    336
Asp Gly Gly Ile Cys Leu Ala Thr Asn Asn Ile Thr Met Lys Lys Asp
            100                 105                 110 ggc agc aac tgt ttt gtc tat gaa att cga ttt gat ggt gtg aac ttt    384
Gly Ser Asn Cys Phe Val Tyr Glu Ile Arg Phe Asp Gly Val Asn Phe
        115                 120                 125 cct gcc aat ggt cca gtt atg cag agg aag acc gtc aaa tgg gag cca    432
Pro Ala Asn Gly Pro Val Met Gln Arg Lys Thr Val Lys Trp Glu Pro
    130                 135                 140 tcc act gag aaa atg tat gtg cgt gat gga gtg ctg aag ggt gat gtt    480
Ser Thr Glu Lys Met Tyr Val Arg Asp Gly Val Leu Lys Gly Asp Val
145                 150                 155                 160 aac atg gct ctg ttg ctt caa gga ggt ggc cat tac cga tgt gac ttc    528
Asn Met Ala Leu Leu Leu Gln Gly Gly Gly His Tyr Arg Cys Asp Phe
                165                 170                 175 aga act act tac aaa gca aag aag gtt gtc cag ttg cca gac tat cac    576
Arg Thr Thr Tyr Lys Ala Lys Lys Val Val Gln Leu Pro Asp Tyr His
            180                 185                 190 ttc gtg gat cat cga att gag ata aca agc cat gac aag gat tac aac    624
Phe Val Asp His Arg Ile Glu Ile Thr Ser His Asp Lys Asp Tyr Asn
        195                 200                 205 aag gtt aag ctg tat gag cat gct aaa gct cat tcc ggg ctg cca agg    672
Lys Val Lys Leu Tyr Glu His Ala Lys Ala His Ser Gly Leu Pro Arg
    210                 215                 220 ctg gcc aag taa                                                    684
Leu Ala Lys
225

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)..(3)
<223> OTHER INFORMATION: Inosine
<220> FEATURE:
<221> NAME/KEY: modified_base
<222> LOCATION: (9)..(9)
<223> OTHER INFORMATION: Inosine
<220> FEATURE:
<221> NAME/KEY: modified_base
<222> LOCATION: (21)..(21)
<223> OTHER INFORMATION: a, c, t, g, unknown or other

<400> SEQUENCE: 3
ggnwsbgtna ayggvcayda ntt                                          23

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aactggaaga attcgcggcc gcaggaa                                      27

<210> SEQ ID NO 5
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (11)..(11)
<223> OTHER INFORMATION: Inosine
<220> FEATURE:
<221> NAME/KEY: modified_base
<222> LOCATION: (14)..(14)
<223> OTHER INFORMATION: Inosine
<220> FEATURE:
<221> NAME/KEY: modified_base
<222> LOCATION: (20)..(20)
<223> OTHER INFORMATION: Inosine

<400> SEQUENCE: 5
tgccwtttgc nttngayatn ttg                                              23

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (4)..(4)
<223> OTHER INFORMATION: Inosine
<220> FEATURE:
<221> NAME/KEY: modified_base
<222> LOCATION: (15)..(15)
<223> OTHER INFORMATION: Inosine
<220> FEATURE:
<221> NAME/KEY: modified_base
<222> LOCATION: (18)..(18)
<223> OTHER INFORMATION: Inosine
<220> FEATURE:
<221> NAME/KEY: modified_base
<222> LOCATION: (21)..(21)
<223> OTHER INFORMATION: Inosine

<400> SEQUENCE: 6
gtcntcttyt gcacnacngg nccatydgva ggaaa                                 35

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(25)
<223> OTHER INFORMATION: Inosine
<220> FEATURE:
<221> NAME/KEY: modified_base
<222> LOCATION: (29)..(30)
<223> OTHER INFORMATION: Inosine
<220> FEATURE:
<221> NAME/KEY: modified_base
<222> LOCATION: (34)..(35)
<223> OTHER INFORMATION: Inosine

<400> SEQUENCE: 7
ggccacgcgt cgactagtac gggnngggnn gggnng                                36

<210> SEQ ID NO 8
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 8
ttgtcaagat atcgaaagcg aacggcagag                                      30

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggccacgcgt cgactagtac                                                 20

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gtccaccctc tacgactttg agttccatat                                      30

<210> SEQ ID NO 11
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cccggatccg atgagtgtga ttacawcaga aatgaagatg gagc                      44

<210> SEQ ID NO 12
<211> LENGTH: 227
<212> TYPE: PRT
<213> ORGANISM: Favia favus

<400> SEQUENCE: 12

Met Ser Val Ile Thr Ser Glu Met Lys Met Glu Leu Arg Met Glu Gly
1               5                   10                  15

Ala Val Asn Gly His Lys Phe Val Ile Thr Gly Lys Gly Ser Gly Gln
            20                  25                  30

Pro Phe Glu Gly Ile Gln Asn Met Asp Leu Thr Val Ile Glu Gly Gly
        35                  40                  45

Pro Leu Pro Phe Ala Phe Asp Ile Leu Thr Thr Val Phe His Tyr Gly
    50                  55                  60

Asn Arg Val Phe Val Lys Tyr Pro Glu Glu Ile Val Asp Tyr Phe Lys
65                  70                  75                  80

Gln Ser Phe Pro Glu Gly Tyr Ser Trp Glu Arg Ser Met Ser Tyr Glu
                85                  90                  95

Asp Gly Gly Ile Cys Leu Ala Thr Asn Asn Ile Thr Met Lys Lys Asp
            100                 105                 110

Gly Ser Asn Cys Phe Val Tyr Glu Ile Arg Phe Asp Gly Val Asn Phe
        115                 120                 125

Pro Ala Asn Gly Pro Val Met Gln Arg Lys Thr Val Lys Trp Glu Pro
```

```
                  130                 135                 140
Ser Thr Glu Lys Met Tyr Val Arg Asp Gly Val Leu Lys Gly Asp Val
145                 150                 155                 160

Asn Met Ala Leu Leu Leu Gln Gly Gly Gly His Tyr Arg Cys Asp Phe
                165                 170                 175

Arg Thr Thr Tyr Lys Ala Lys Lys Val Val Gln Leu Pro Asp Tyr His
            180                 185                 190

Phe Val Asp His Arg Ile Glu Ile Thr Ser His Asp Lys Asp Tyr Asn
        195                 200                 205

Lys Val Lys Leu Tyr Glu His Ala Lys Ala His Ser Gly Leu Pro Arg
    210                 215                 220

Leu Ala Lys
225

<210> SEQ ID NO 13
<211> LENGTH: 684
<212> TYPE: DNA
<213> ORGANISM: Favia favus
<220> FEATURE:
<221> NAME/KEY: CDS
<222> LOCATION: (1)..(681)

<400> SEQUENCE: 13 atg agt gtg att aca tca gaa atg aag atg gag ctg cgt atg gaa ggc      48
Met Ser Val Ile Thr Ser Glu Met Lys Met Glu Leu Arg Met Glu Gly
1               5                   10                  15 gct gta aac ggg cac aag ttc gtg att aca ggg aaa gga agt ggc cag      96
Ala Val Asn Gly His Lys Phe Val Ile Thr Gly Lys Gly Ser Gly Gln
            20                  25                  30 cct ttc gag gga ata cag aat atg gac ctg aca gtc ata gag ggc gga     144
Pro Phe Glu Gly Ile Gln Asn Met Asp Leu Thr Val Ile Glu Gly Gly
        35                  40                  45 cct ctt cct ttt gct ttc gat atc ctg aca aca gta ttc cat tac ggc     192
Pro Leu Pro Phe Ala Phe Asp Ile Leu Thr Thr Val Phe His Tyr Gly
    50                  55                  60 aac cgg gta ttt gtc aaa tac cca gaa gaa ata gta gac tac ttc aag     240
Asn Arg Val Phe Val Lys Tyr Pro Glu Glu Ile Val Asp Tyr Phe Lys
65                  70                  75                  80 cag tcg ttt cct gag ggt tat tct tgg gaa cga agc atg agt tac gaa     288
Gln Ser Phe Pro Glu Gly Tyr Ser Trp Glu Arg Ser Met Ser Tyr Glu
                85                  90                  95 gac ggg gga att tgc ctc gcc aca aac aat ata acg atg aag aaa gac     336
Asp Gly Gly Ile Cys Leu Ala Thr Asn Asn Ile Thr Met Lys Lys Asp
            100                 105                 110 ggc agc aac tgt ttt gtc tat gaa att cga ttt gat ggt gtg aac ttt     384
Gly Ser Asn Cys Phe Val Tyr Glu Ile Arg Phe Asp Gly Val Asn Phe
        115                 120                 125 cct gcc aat ggt cca gtt atg cag agg aag acc gtc aaa tgg gag cca     432
Pro Ala Asn Gly Pro Val Met Gln Arg Lys Thr Val Lys Trp Glu Pro
    130                 135                 140 tcc act gag aaa atg tat gtg cgt gat gga gtg ctg aag ggt gat gtt     480
Ser Thr Glu Lys Met Tyr Val Arg Asp Gly Val Leu Lys Gly Asp Val
145                 150                 155                 160 aac atg gct ctg ttg ctt caa gga ggt ggc cat tac cga tgt gac ttc     528
Asn Met Ala Leu Leu Leu Gln Gly Gly Gly His Tyr Arg Cys Asp Phe
                165                 170                 175 aga act act tac aaa gca aag aag gtt gtc cag ttg cca gac tat cac     576
Arg Thr Thr Tyr Lys Ala Lys Lys Val Val Gln Leu Pro Asp Tyr His
            180                 185                 190 ttc gtg gat cat cga att gag ata aca agc cat gac aag gat tac aac     624
```

```
                    Phe Val Asp His Arg Ile Glu Ile Thr Ser His Asp Lys Asp Tyr Asn
                                    195                 200                 205 aag gtt aag ctg tat gag cat gct aaa gct cat tcc ggg ctg cca agg           672
Lys Val Lys Leu Tyr Glu His Ala Lys Ala His Ser Gly Leu Pro Arg
    210                 215                 220 ctg gcc aag taa                                                            684
Leu Ala Lys
225
```

<210> SEQ ID NO 14
<211> LENGTH: 227
<212> TYPE: PRT
<213> ORGANISM: Favia favus

<400> SEQUENCE: 14

```
Met Ser Val Ile Thr Ser Glu Met Lys Met Glu Leu Arg Met Glu Gly
1               5                   10                  15

Ala Val Asn Gly His Lys Phe Val Ile Thr Gly Lys Gly Ser Gly Gln
            20                  25                  30

Pro Phe Glu Gly Ile Gln Asn Val Asp Leu Thr Val Ile Glu Gly Gly
        35                  40                  45

Pro Leu Pro Phe Ala Phe Asp Ile Leu Thr Thr Val Phe His Tyr Gly
    50                  55                  60

Asn Arg Val Phe Val Lys Tyr Pro Glu Ile Val Asp Tyr Phe Lys
65                  70                  75                  80

Gln Ser Phe Pro Glu Gly Tyr Ser Trp Glu Arg Ser Met Ser Tyr Glu
                85                  90                  95

Asp Gly Gly Ile Cys Leu Ala Thr Asn Asn Ile Thr Met Lys Lys Asp
            100                 105                 110

Gly Ser Asn Cys Phe Val Tyr Glu Ile Arg Phe Asp Gly Val Asn Phe
        115                 120                 125

Pro Ala Asn Gly Pro Val Met Gln Arg Lys Thr Val Lys Trp Glu Pro
    130                 135                 140

Ser Thr Glu Lys Met Tyr Val Arg Asp Gly Val Leu Lys Gly Asp Val
145                 150                 155                 160

Asn Met Ala Leu Leu Leu Gln Gly Gly Gly His Tyr Arg Cys Asp Phe
                165                 170                 175

Arg Thr Thr Tyr Lys Ala Lys Lys Val Val Gln Leu Pro Asp Tyr His
            180                 185                 190

Phe Val Asp His Arg Met Glu Ile Thr Ser His Asp Lys Asp Tyr Asn
        195                 200                 205

Lys Val Lys Leu Tyr Glu His Ala Lys Ala His Ser Gly Leu Pro Arg
    210                 215                 220

Leu Ala Lys
225
```

<210> SEQ ID NO 15
<211> LENGTH: 684
<212> TYPE: DNA
<213> ORGANISM: Favia favus
<220> FEATURE:
<221> NAME/KEY: CDS
<222> LOCATION: (1)..(681)

<400> SEQUENCE: 15

```
atg agt gtg att aca tca gaa atg aag atg gag ctg cgt atg gaa ggc           48
Met Ser Val Ile Thr Ser Glu Met Lys Met Glu Leu Arg Met Glu Gly
1               5                   10                  15 gct gta aac ggg cac aag ttc gtg att aca ggg aaa gga agt ggc cag            96
```

```
                  Ala Val Asn Gly His Lys Phe Val Ile Thr Gly Lys Gly Ser Gly Gln
                           20                  25                  30 cct ttc gag gga ata cag aat gtg gac ctg aca gtc ata gag ggc gga           144
Pro Phe Glu Gly Ile Gln Asn Val Asp Leu Thr Val Ile Glu Gly Gly
         35                  40                  45 cct ctt cct ttt gct ttc gat atc ctg aca aca gta ttc cat tac ggc           192
Pro Leu Pro Phe Ala Phe Asp Ile Leu Thr Thr Val Phe His Tyr Gly
 50                  55                  60 aac cgg gta ttt gtc aaa tac cca gaa gaa ata gta gac tac ttc aag           240
Asn Arg Val Phe Val Lys Tyr Pro Glu Glu Ile Val Asp Tyr Phe Lys
 65                  70                  75                  80 cag tcg ttt cct gag ggt tat tct tgg gaa cga agc atg agt tac gaa           288
Gln Ser Phe Pro Glu Gly Tyr Ser Trp Glu Arg Ser Met Ser Tyr Glu
             85                  90                  95 gac ggg gga att tgc ctc gcc aca aac aat ata acg atg aag aaa gac           336
Asp Gly Gly Ile Cys Leu Ala Thr Asn Asn Ile Thr Met Lys Lys Asp
        100                 105                 110 ggc agc aac tgt ttt gtc tat gaa att cga ttt gat ggt gtg aac ttt           384
Gly Ser Asn Cys Phe Val Tyr Glu Ile Arg Phe Asp Gly Val Asn Phe
        115                 120                 125 cct gcc aat ggt cca gtt atg cag agg aag acc gtc aaa tgg gag cca           432
Pro Ala Asn Gly Pro Val Met Gln Arg Lys Thr Val Lys Trp Glu Pro
130                 135                 140 tcc act gag aaa atg tat gtg cgt gat gga gtg ctg aag ggt gat gtt           480
Ser Thr Glu Lys Met Tyr Val Arg Asp Gly Val Leu Lys Gly Asp Val
145                 150                 155                 160 aac atg gct ctg ttg ctt caa gga ggt ggc cat tac cga tgt gac ttc           528
Asn Met Ala Leu Leu Leu Gln Gly Gly Gly His Tyr Arg Cys Asp Phe
                165                 170                 175 aga act act tac aaa gca aag aag gtt gtc cag ttg cca gac tat cac           576
Arg Thr Thr Tyr Lys Ala Lys Lys Val Val Gln Leu Pro Asp Tyr His
            180                 185                 190 ttc gtg gat cat cga atg gag ata aca agc cat gac aag gat tac aac           624
Phe Val Asp His Arg Met Glu Ile Thr Ser His Asp Lys Asp Tyr Asn
        195                 200                 205 aag gtt aag ctg tat gag cat gct aaa gct cat tcc ggg ctg cca agg           672
Lys Val Lys Leu Tyr Glu His Ala Lys Ala His Ser Gly Leu Pro Arg
        210                 215                 220 ctg gcc aag taa                                                           684
Leu Ala Lys
225

<210> SEQ ID NO 16
<211> LENGTH: 227
<212> TYPE: PRT
<213> ORGANISM: Favia favus

<400> SEQUENCE: 16

Met Ser Val Ile Thr Ser Glu Met Lys Ile Glu Val Arg Met Glu Gly
1               5                   10                  15

Ala Val Asn Gly His Lys Phe Val Ile Thr Gly Lys Gly Ser Gly Gln
            20                  25                  30

Pro Phe Glu Gly Ile Gln Asn Val Asp Leu Thr Val Ile Glu Gly Gly
        35                  40                  45

Pro Leu Pro Phe Ala Phe Asp Ile Leu Thr Thr Ala Phe His Tyr Gly
    50                  55                  60

Asn Arg Val Phe Val Lys Tyr Pro Glu Glu Ile Val Asp Tyr Phe Lys
65                  70                  75                  80

Gln Ser Phe Pro Glu Gly Tyr Ser Trp Glu Arg Ser Met Ser Tyr Glu
                85                  90                  95
```

```
Asp Gly Gly Ile Cys Leu Ala Thr Asn Asn Ile Thr Met Lys Lys Asp
            100                 105                 110

Gly Ser Asn Cys Phe Val Asn Glu Ile Arg Phe Asp Gly Val Asn Phe
        115                 120                 125

Pro Ala Asn Gly Pro Val Met Gln Arg Lys Thr Val Lys Trp Glu Ser
    130                 135                 140

Ser Thr Glu Lys Met Tyr Val Arg Asp Gly Val Leu Lys Gly Asp Val
145                 150                 155                 160

Asn Met Ala Leu Leu Leu Gln Gly Gly Gly His Tyr Arg Cys Asp Phe
                165                 170                 175

Arg Thr Thr Tyr Lys Ala Lys Lys Val Val Gln Leu Pro Asp Tyr His
            180                 185                 190

Phe Val Asp His Leu Met Glu Ile Thr Ser His Asp Lys Asp Tyr Asn
        195                 200                 205

Lys Val Lys Leu Tyr Glu His Ala Lys Ala His Ser Gly Leu Pro Arg
    210                 215                 220

Leu Ala Lys
225

<210> SEQ ID NO 17
<211> LENGTH: 684
<212> TYPE: DNA
<213> ORGANISM: Favia favus
<220> FEATURE:
<221> NAME/KEY: CDS
<222> LOCATION: (1)..(681)

<400> SEQUENCE: 17 atg agt gtg att aca tca gaa atg aag atc gag gtg cgt atg gaa ggc    48
Met Ser Val Ile Thr Ser Glu Met Lys Ile Glu Val Arg Met Glu Gly
1               5                   10                  15 gct gta aac ggg cac aag ttc gtg att aca ggg aaa gga agt ggc cag    96
Ala Val Asn Gly His Lys Phe Val Ile Thr Gly Lys Gly Ser Gly Gln
            20                  25                  30 cct ttc gag gga ata cag aat gtg gac ctg aca gtc ata gag ggc gga   144
Pro Phe Glu Gly Ile Gln Asn Val Asp Leu Thr Val Ile Glu Gly Gly
        35                  40                  45 cct ctt cct ttt gct ttc gat atc ctg aca aca gca ttc cat tac ggc   192
Pro Leu Pro Phe Ala Phe Asp Ile Leu Thr Thr Ala Phe His Tyr Gly
    50                  55                  60 aac cgg gta ttt gtc aaa tac cca gaa gaa ata gta gac tac ttc aag   240
Asn Arg Val Phe Val Lys Tyr Pro Glu Glu Ile Val Asp Tyr Phe Lys
65                  70                  75                  80 cag tcg ttt cct gag ggt tat tct tgg gaa cga agc atg agt tac gaa   288
Gln Ser Phe Pro Glu Gly Tyr Ser Trp Glu Arg Ser Met Ser Tyr Glu
                85                  90                  95 gac ggg gga att tgc ctc gcc aca aac aat ata acg atg aag aaa gac   336
Asp Gly Gly Ile Cys Leu Ala Thr Asn Asn Ile Thr Met Lys Lys Asp
            100                 105                 110 ggc agc aac tgt ttt gtc aat gaa att cga ttt gat ggt gtg aac ttt   384
Gly Ser Asn Cys Phe Val Asn Glu Ile Arg Phe Asp Gly Val Asn Phe
        115                 120                 125 cct gcc aat ggt cca gtt atg cag agg aag acc gtc aaa tgg gag tca   432
Pro Ala Asn Gly Pro Val Met Gln Arg Lys Thr Val Lys Trp Glu Ser
    130                 135                 140 tcc act gag aaa atg tat gtg cgt gat gga gtg ctg aag ggt gat gtt   480
Ser Thr Glu Lys Met Tyr Val Arg Asp Gly Val Leu Lys Gly Asp Val
145                 150                 155                 160 aac atg gct ctg ttg ctt caa gga ggt ggc cat tac cga tgt gac ttc   528
```

```
                                                              -continued

Asn Met Ala Leu Leu Leu Gln Gly Gly Gly His Tyr Arg Cys Asp Phe
            165                 170                 175 aga act act tac aaa gca aag aag gtt gtc cag ttg cca gac tat cac      576
Arg Thr Thr Tyr Lys Ala Lys Lys Val Val Gln Leu Pro Asp Tyr His
        180                 185                 190 ttc gtg gat cat cta atg gag ata aca agc cat gac aag gat tac aac      624
Phe Val Asp His Leu Met Glu Ile Thr Ser His Asp Lys Asp Tyr Asn
            195                 200                 205 aag gtt aag ctg tat gag cat gct aaa gct cat tcc ggg ctg cca agg      672
Lys Val Lys Leu Tyr Glu His Ala Lys Ala His Ser Gly Leu Pro Arg
        210                 215                 220 ctg gcc aag taa                                                       684
Leu Ala Lys
225

<210> SEQ ID NO 18
<211> LENGTH: 227
<212> TYPE: PRT
<213> ORGANISM: Favia favus

<400> SEQUENCE: 18

Met Ser Val Ile Thr Ser Glu Met Lys Ile Glu Leu Arg Met Glu Gly
1               5                   10                  15

Ala Val Asn Gly His Lys Phe Val Ile Thr Gly Lys Gly Ser Gly Gln
            20                  25                  30

Pro Phe Glu Gly Ile Gln Asn Val Asp Leu Thr Val Ile Glu Gly Gly
        35                  40                  45

Pro Leu Pro Phe Ala Phe Asp Ile Leu Thr Thr Ala Phe His Tyr Gly
    50                  55                  60

Asn Arg Val Phe Val Glu Tyr Pro Glu Glu Ile Val Asp Tyr Phe Lys
65                  70                  75                  80

Gln Ser Phe Pro Glu Gly Tyr Ser Trp Glu Arg Ser Met Ser Tyr Glu
                85                  90                  95

Asp Gly Gly Ile Cys Leu Ala Thr Asn Asn Ile Thr Met Lys Lys Asp
            100                 105                 110

Gly Ser Asn Cys Phe Val Asn Glu Ile Arg Phe Asp Gly Val Asn Phe
        115                 120                 125

Pro Ala Asn Gly Pro Val Met Gln Arg Lys Thr Val Lys Trp Glu Pro
    130                 135                 140

Ser Thr Glu Lys Met Tyr Val Arg Asp Gly Val Leu Lys Gly Asp Val
145                 150                 155                 160

Asn Met Ala Leu Leu Leu Gln Gly Gly Gly His Tyr Arg Cys Asp Phe
                165                 170                 175

Arg Thr Thr Tyr Lys Ala Lys Lys Val Val Gln Leu Pro Asp Tyr His
            180                 185                 190

Phe Val Asp His Gln Met Glu Ile Thr Ser His Asp Lys Asp Tyr Asn
        195                 200                 205

Lys Val Lys Leu Tyr Glu His Ala Lys Ala His Ser Gly Leu Pro Arg
    210                 215                 220

Leu Ala Lys
225

<210> SEQ ID NO 19
<211> LENGTH: 684
<212> TYPE: DNA
<213> ORGANISM: Favia favus
<220> FEATURE:
<221> NAME/KEY: CDS
<222> LOCATION: (1)..(681)
```

```
<400> SEQUENCE: 19 atg agt gtg att aca tca gaa atg aag atc gag ctg cgt atg gaa ggc      48
Met Ser Val Ile Thr Ser Glu Met Lys Ile Glu Leu Arg Met Glu Gly
1               5                   10                  15 gct gta aac ggg cac aag ttc gtg att aca ggg aaa gga agt ggc cag      96
Ala Val Asn Gly His Lys Phe Val Ile Thr Gly Lys Gly Ser Gly Gln
                20                  25                  30 cct ttc gag gga ata cag aat gtg gac ctg aca gtc ata gag ggc gga     144
Pro Phe Glu Gly Ile Gln Asn Val Asp Leu Thr Val Ile Glu Gly Gly
            35                  40                  45 cct ctt cct ttt gct ttc gat atc ctg aca aca gca ttc cat tac ggc     192
Pro Leu Pro Phe Ala Phe Asp Ile Leu Thr Thr Ala Phe His Tyr Gly
        50                  55                  60 aac cgg gta ttt gtc gaa tac cca gaa gaa ata gta gac tac ttc aag     240
Asn Arg Val Phe Val Glu Tyr Pro Glu Glu Ile Val Asp Tyr Phe Lys
65                  70                  75                  80 cag tcg ttt cct gag ggt tat tct tgg gaa cga agc atg agt tac gaa     288
Gln Ser Phe Pro Glu Gly Tyr Ser Trp Glu Arg Ser Met Ser Tyr Glu
                85                  90                  95 gac ggg gga att tgc ctc gcc aca aac aat ata acg atg aag aaa gac     336
Asp Gly Gly Ile Cys Leu Ala Thr Asn Asn Ile Thr Met Lys Lys Asp
                100                 105                 110 ggc agc aac tgt ttt gtc aat gaa att cga ttt gat ggt gtg aac ttt     384
Gly Ser Asn Cys Phe Val Asn Glu Ile Arg Phe Asp Gly Val Asn Phe
            115                 120                 125 cct gcc aat ggt cca gtt atg cag agg aag acc gtc aaa tgg gag cca     432
Pro Ala Asn Gly Pro Val Met Gln Arg Lys Thr Val Lys Trp Glu Pro
        130                 135                 140 tcc act gag aaa atg tat gtg cgt gat gga gtg ctg aag ggt gat gta     480
Ser Thr Glu Lys Met Tyr Val Arg Asp Gly Val Leu Lys Gly Asp Val
145                 150                 155                 160 aac atg gct ctg ttg ctt caa gga ggt ggc cat tac cga tgt gac ttc     528
Asn Met Ala Leu Leu Leu Gln Gly Gly Gly His Tyr Arg Cys Asp Phe
                165                 170                 175 aga act act tac aaa gca aag aag gtt gtc cag ttg cca gac tat cac     576
Arg Thr Thr Tyr Lys Ala Lys Lys Val Val Gln Leu Pro Asp Tyr His
                180                 185                 190 ttc gtg gat cat caa atg gag ata aca agc cat gac aag gat tac aac     624
Phe Val Asp His Gln Met Glu Ile Thr Ser His Asp Lys Asp Tyr Asn
            195                 200                 205 aag gtt aag ctg tat gag cat gct aaa gct cat tcc ggg ctg cca agg     672
Lys Val Lys Leu Tyr Glu His Ala Lys Ala His Ser Gly Leu Pro Arg
        210                 215                 220 ctg gcc aag taa                                                     684
Leu Ala Lys
225

<210> SEQ ID NO 20
<211> LENGTH: 227
<212> TYPE: PRT
<213> ORGANISM: Favia favus

<400> SEQUENCE: 20

Met Ser Val Ile Thr Ser Glu Met Lys Met Glu Leu Arg Met Glu Gly
1               5                   10                  15

Ala Val Asn Gly His Lys Phe Val Ile Thr Gly Lys Gly Ser Gly Gln
                20                  25                  30

Pro Phe Glu Gly Ile Gln Asn Met Asp Leu Thr Val Ile Glu Gly Gly
            35                  40                  45
```

```
Pro Leu Pro Phe Ala Phe Asp Ile Leu Thr Thr Ala Phe Gly His Gly
    50                  55                  60

Asn Arg Val Phe Val Lys Tyr Pro Glu Glu Ile Val Asp Tyr Phe Lys
 65                  70                  75                  80

Gln Ser Phe Pro Glu Gly Tyr Ser Trp Glu Arg Ser Met Ser Tyr Glu
                 85                  90                  95

Asp Gly Gly Ile Cys Leu Ala Thr Asn Asn Ile Thr Met Lys Lys Asp
            100                 105                 110

Gly Ser Asn Cys Phe Val Tyr Glu Ile Arg Phe Asp Gly Val Asn Phe
        115                 120                 125

Pro Ala Asn Gly Pro Val Met Gln Arg Lys Thr Val Lys Trp Glu Pro
    130                 135                 140

Ser Thr Glu Lys Met Tyr Val Arg Asp Gly Val Leu Lys Gly Asp Val
145                 150                 155                 160

Asn Met Ala Leu Leu Leu Gln Gly Gly Gly His Tyr Arg Cys Asp Phe
                165                 170                 175

Arg Thr Thr Tyr Lys Ala Lys Lys Val Val Gln Leu Pro Asp Tyr His
            180                 185                 190

Phe Val Asp Leu Arg Thr Glu Ile Thr Ser His Asp Lys Asp Tyr Asn
        195                 200                 205

Lys Val Lys Leu Tyr Glu His Ala Lys Ala His Ser Gly Leu Pro Arg
    210                 215                 220

Leu Ala Lys
225

<210> SEQ ID NO 21
<211> LENGTH: 684
<212> TYPE: DNA
<213> ORGANISM: Favia favus
<220> FEATURE:
<221> NAME/KEY: CDS
<222> LOCATION: (1)..(681)

<400> SEQUENCE: 21 atg agt gtg att aca tca gaa atg aag atg gag ctg cgt atg gaa ggc     48
Met Ser Val Ile Thr Ser Glu Met Lys Met Glu Leu Arg Met Glu Gly
 1               5                  10                  15 gct gta aac ggg cac aag ttc gtg att aca ggg aaa gga agt ggc cag     96
Ala Val Asn Gly His Lys Phe Val Ile Thr Gly Lys Gly Ser Gly Gln
                20                  25                  30 cct ttc gag gga ata cag aat atg gac ctg aca gtc ata gag ggc gga    144
Pro Phe Glu Gly Ile Gln Asn Met Asp Leu Thr Val Ile Glu Gly Gly
            35                  40                  45 cct ctt cct ttt gct ttc gat atc ctg aca aca gca ttc ggt cac ggc    192
Pro Leu Pro Phe Ala Phe Asp Ile Leu Thr Thr Ala Phe Gly His Gly
    50                  55                  60 aac cgg gta ttt gtc aaa tac cca gaa gaa ata gta gac tac ttc aag    240
Asn Arg Val Phe Val Lys Tyr Pro Glu Glu Ile Val Asp Tyr Phe Lys
 65                  70                  75                  80 cag tcg ttt cct gag ggt tat tct tgg gaa cga agc atg agt tac gaa    288
Gln Ser Phe Pro Glu Gly Tyr Ser Trp Glu Arg Ser Met Ser Tyr Glu
                 85                  90                  95 gac ggg gga att tgc ctc gcc aca aac aat ata acg atg aag aaa gac    336
Asp Gly Gly Ile Cys Leu Ala Thr Asn Asn Ile Thr Met Lys Lys Asp
            100                 105                 110 ggc agc aac tgt ttt gtc tat gaa att cga ttt gat ggt gtg aac ttt    384
Gly Ser Asn Cys Phe Val Tyr Glu Ile Arg Phe Asp Gly Val Asn Phe
        115                 120                 125 cct gcc aat ggt cca gtt atg cag agg aag acc gtc aaa tgg gag cca    432
```

```
               Pro Ala Asn Gly Pro Val Met Gln Arg Lys Thr Val Lys Trp Glu Pro
                   130                 135                 140 tcc act gag aaa atg tat gtg cgt gat gga gtg ctg aag ggt gat gtt         480
Ser Thr Glu Lys Met Tyr Val Arg Asp Gly Val Leu Lys Gly Asp Val
145                 150                 155                 160 aac atg gct ctg ttg ctt caa gga ggt ggc cat tac cga tgt gac ttc         528
Asn Met Ala Leu Leu Leu Gln Gly Gly Gly His Tyr Arg Cys Asp Phe
                165                 170                 175 aga act act tac aaa gca aag aag gtt gtc cag ttg cca gac tat cac         576
Arg Thr Thr Tyr Lys Ala Lys Lys Val Val Gln Leu Pro Asp Tyr His
            180                 185                 190 ttc gtg gat ctt cga act gag ata aca agc cat gac aag gat tac aac         624
Phe Val Asp Leu Arg Thr Glu Ile Thr Ser His Asp Lys Asp Tyr Asn
        195                 200                 205 aag gtt aag ctg tat gag cat gct aaa gct cat tcc ggg ctg cca agg         672
Lys Val Lys Leu Tyr Glu His Ala Lys Ala His Ser Gly Leu Pro Arg
    210                 215                 220 ctg gcc aag taa                                                         684
Leu Ala Lys
225

<210> SEQ ID NO 22
<211> LENGTH: 225
<212> TYPE: PRT
<213> ORGANISM: Discosoma sp.

<400> SEQUENCE: 22

Met Arg Ser Ser Lys Asn Val Ile Lys Glu Phe Met Arg Phe Lys Val
1               5                   10                  15

Arg Met Glu Gly Thr Val Asn Gly His Glu Phe Glu Ile Glu Gly Glu
            20                  25                  30

Gly Glu Gly Arg Pro Tyr Glu Gly His Asn Thr Val Lys Leu Lys Val
        35                  40                  45

Thr Lys Gly Gly Pro Leu Pro Phe Ala Trp Asp Ile Leu Ser Pro Gln
    50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Cys Phe Ile Tyr Lys Val Lys Phe Ile Gly Val Asn
        115                 120                 125

Phe Pro Ser Asp Gly Pro Val Met Gln Lys Lys Thr Met Gly Trp Glu
    130                 135                 140

Ala Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ser Lys Leu Asp Ile Thr Ser His Asn Glu Asp Tyr
        195                 200                 205

Thr Ile Val Glu Gln Tyr Glu Arg Thr Glu Gly Arg His His Leu Phe
    210                 215                 220

Leu
225
```

```
<210> SEQ ID NO 23
<211> LENGTH: 225
<212> TYPE: PRT
<213> ORGANISM: Trachyphyllia geoffroyi

<400> SEQUENCE: 23

Met Ser Leu Ile Lys Pro Glu Met Lys Ile Lys Leu Leu Met Glu Gly
1               5                   10                  15

Asn Val Asn Gly His Gln Phe Val Ile Glu Gly Asp Gly Lys Gly His
            20                  25                  30

Pro Phe Glu Gly Lys Gln Ser Met Asp Leu Val Val Lys Glu Gly Ala
        35                  40                  45

Pro Leu Pro Phe Ala Tyr Asp Ile Leu Thr Thr Ala Phe His Tyr Gly
    50                  55                  60

Asn Arg Val Phe Ala Lys Tyr Pro Asp His Ile Pro Asp Tyr Phe Lys
65                  70                  75                  80

Gln Ser Phe Pro Lys Gly Phe Ser Trp Glu Arg Ser Leu Met Phe Glu
                85                  90                  95

Asp Gly Gly Val Cys Ile Ala Thr Asn Asp Ile Thr Leu Lys Gly Asp
            100                 105                 110

Thr Phe Phe Asn Lys Val Arg Phe Asp Gly Val Asn Phe Pro Pro Asn
        115                 120                 125

Gly Pro Val Met Gln Lys Lys Thr Leu Lys Trp Glu Ala Ser Thr Glu
    130                 135                 140

Lys Met Tyr Leu Arg Asp Gly Val Leu Thr Gly Asp Ile Thr Met Ala
145                 150                 155                 160

Leu Leu Leu Lys Gly Asp Val His Tyr Arg Cys Asp Phe Arg Thr Thr
                165                 170                 175

Tyr Lys Ser Arg Gln Glu Gly Val Lys Leu Pro Gly Tyr His Phe Val
            180                 185                 190

Asp His Cys Ile Ser Ile Leu Arg His Asp Lys Asp Tyr Asn Glu Val
        195                 200                 205

Lys Leu Tyr Glu His Ala Val Ala His Ser Gly Leu Pro Asp Asn Val
    210                 215                 220

Lys
225
```